US008946403B2

(12) United States Patent
Tolentino et al.

(10) Patent No.: US 8,946,403 B2
(45) Date of Patent: *Feb. 3, 2015

(54) COMPOSITIONS AND METHODS FOR SIRNA INHIBITION OF ANGIOGENESIS

(71) Applicant: The Trustees of the University of Pennsylvania, Philadelphia, PA (US)

(72) Inventors: Michael J. Tolentino, Villanova, PA (US); Samuel Jotham Reich, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,040

(22) Filed: Sep. 30, 2013

(65) Prior Publication Data

US 2014/0056969 A1    Feb. 27, 2014

Related U.S. Application Data

(60) Continuation of application No. 11/422,982, filed on Jun. 8, 2006, now Pat. No. 8,546,345, which is a division of application No. 10/294,228, filed on Nov. 14, 2002, now Pat. No. 7,148,342.

(60) Provisional application No. 60/398,417, filed on Jul. 24, 2002.

(51) Int. Cl.
  *C07H 21/02*    (2006.01)
  *C07H 21/04*    (2006.01)

(52) U.S. Cl.
  USPC ........................ 536/24.5; 536/23.1

(58) Field of Classification Search
  USPC ............................ 514/44; 536/24.5
  See application file for complete search history.

(56) References Cited

U.S. PATENT DOCUMENTS

| | | | |
|---|---|---|---|
| 4,235,871 A | 11/1980 | Papahadjopoulos et al. |
| 4,394,448 A | 7/1983 | Szoka, Jr. et al. |
| 4,501,728 A | 2/1985 | Geho et al. |
| 4,670,388 A | 6/1987 | Rubin et al. |
| 4,837,028 A | 6/1989 | Allen |
| 4,920,016 A | 4/1990 | Allen et al. |
| 5,019,369 A | 5/1991 | Presant et al. |

(Continued)

FOREIGN PATENT DOCUMENTS

| | | |
|---|---|---|
| CA | 2359180 A1 | 8/2000 |
| EP | 0308066 A2 | 3/1989 |

(Continued)

OTHER PUBLICATIONS

Acheampong, et al., Distribution of Brimonidine into Anterior and Posterior Tissues of Monkey, Rabbit, and Rat Eyes, *Drug Metabol. ISM & Disposition* (Apr. 1, 2002), 30(4):421-429.

(Continued)

*Primary Examiner* — Terra Cotta Gibbs
(74) *Attorney, Agent, or Firm* — Pepper Hamilton LLP

(57) ABSTRACT

RNA interference using small interfering RNAs which are specific for the vascular endothelial growth factor (VEGF) gene and the VEGF receptor genes Flt-1 and Flk-1/KDR inhibit expression of these genes. Diseases which involve angiogenesis stimulated by overexpression of VEGF, such as diabetic retinopathy, age related macular degeneration and many types of cancer, can be treated by administering the small interfering RNAs.

10 Claims, 5 Drawing Sheets

(56) References Cited

U.S. PATENT DOCUMENTS

| | | |
|---|---|---|
| 5,139,941 A | 8/1992 | Muzyczka et al. |
| 5,252,479 A | 10/1993 | Srivastava |
| 5,322,933 A | 6/1994 | Davies et al. |
| 5,498,521 A | 3/1996 | Dryja et al. |
| 5,550,289 A | 8/1996 | Eppstein et al. |
| 5,580,859 A | 12/1996 | Felgner et al. |
| 5,588,961 A | 12/1996 | Leone et al. |
| 5,589,466 A | 12/1996 | Felgner et al. |
| 5,624,803 A | 4/1997 | Noonberg et al. |
| 5,639,736 A | 6/1997 | Robinson |
| 5,639,872 A | 6/1997 | Robinson |
| 5,661,135 A | 8/1997 | Robinson |
| 5,683,986 A | 11/1997 | Carter |
| 5,712,257 A | 1/1998 | Carter |
| 5,728,068 A | 3/1998 | Leone et al. |
| 5,801,156 A | 9/1998 | Robinson et al. |
| 5,814,620 A | 9/1998 | Robinson et al. |
| 5,843,016 A | 12/1998 | Lugnani et al. |
| 5,902,598 A | 5/1999 | Chen et al. |
| 6,015,894 A | 1/2000 | Bennett et al. |
| 6,020,462 A | 2/2000 | Semenza |
| 6,037,329 A | 3/2000 | Baird et al. |
| 6,121,000 A | 9/2000 | Wright et al. |
| 6,150,092 A | 11/2000 | Uchida et al. |
| 6,165,709 A | 12/2000 | Friend et al. |
| 6,177,401 B1 | 1/2001 | Ulrigh et al. |
| 6,219,557 B1 | 4/2001 | Havinis |
| 6,331,313 B1 | 12/2001 | Wong et al. |
| 6,355,271 B1 | 3/2002 | Bell et al. |
| 6,375,972 B1 | 4/2002 | Guo et al. |
| 6,433,145 B1 | 8/2002 | LaFleur et al. |
| 6,506,559 B1 | 1/2003 | Fire et al. |
| 6,852,510 B2 | 2/2005 | Bremel et al. |
| 7,056,704 B2 | 6/2006 | Tuschl et al. |
| 7,090,864 B2 | 8/2006 | Pardridge et al. |
| 7,148,342 B2 | 12/2006 | Tolentino et al. |
| 7,176,303 B2 | 2/2007 | Frier et al. |
| 7,199,107 B2 | 4/2007 | Dobie et al. |
| 7,345,027 B2 | 3/2008 | Tolentino et al. |
| 7,468,431 B2 | 12/2008 | Bhanot et al. |
| 7,674,895 B2 | 3/2010 | Reich et al. |
| 7,709,628 B2 | 5/2010 | Freier et al. |
| 7,750,143 B2 | 7/2010 | Tolentino et al. |
| 8,202,845 B2 | 6/2012 | Drumm et al. |
| 8,541,384 B2 * | 9/2013 | Tolentino et al. ............ 514/44 A |
| 2001/0021772 A1 | 9/2001 | Uhlmann et al. |
| 2002/0054902 A1 | 5/2002 | Pardridge |
| 2002/0086356 A1 | 7/2002 | Tuschl et al. |
| 2002/0132788 A1 | 9/2002 | Lewis et al. |
| 2002/0162126 A1 | 10/2002 | Beach et al. |
| 2002/0165158 A1 | 11/2002 | King |
| 2002/0173478 A1 | 11/2002 | Gewirtz |
| 2002/0183683 A1 | 12/2002 | Lerner |
| 2003/0138407 A1 | 7/2003 | Lu et al. |
| 2003/0153519 A1 | 8/2003 | Kay et al. |
| 2003/0216335 A1 | 11/2003 | Lockridge et al. |
| 2004/0018176 A1 | 1/2004 | Tolentino et al. |
| 2004/0018716 A1 | 1/2004 | Kitou et al. |
| 2004/0096848 A1 | 5/2004 | Thru et al. |
| 2004/0115640 A1 | 6/2004 | Myers et al. |
| 2004/0180357 A1 | 9/2004 | Reich et al. |
| 2004/0220129 A1 | 11/2004 | Reich et al. |
| 2004/0248174 A1 | 12/2004 | Reich et al. |
| 2004/0259247 A1 | 12/2004 | Tuschl et al. |
| 2005/0019927 A1 | 1/2005 | Hildinger et al. |
| 2005/0048529 A1 | 3/2005 | McSwiggen |
| 2005/0159380 A1 | 7/2005 | Guerciolini et al. |
| 2005/0187174 A1 | 8/2005 | Richards et al. |
| 2005/0197315 A1 | 9/2005 | Taira et al. |
| 2005/0222061 A1 | 10/2005 | Schulte |
| 2005/0246794 A1 | 11/2005 | Khvorova et al. |
| 2006/0003915 A1 | 1/2006 | Drumm et al. |
| 2006/0094032 A1 | 5/2006 | Fougerolles et al. |
| 2006/0182783 A1 | 8/2006 | Hughes et al. |
| 2006/0217332 A1 | 9/2006 | Vargeese et al. |
| 2006/0223770 A1 | 10/2006 | Fougerolles et al. |
| 2006/0286073 A1 | 12/2006 | Tolentino et al. |
| 2006/0292120 A1 | 12/2006 | Tolentino et al. |
| 2007/0003523 A1 | 1/2007 | Tolentino et al. |
| 2007/0037760 A1 | 2/2007 | Tolentino et al. |
| 2007/0037761 A1 | 2/2007 | Tolentino et al. |
| 2007/0037762 A1 | 2/2007 | Tolentino et al. |
| 2007/0149471 A1 | 6/2007 | Reich et al. |
| 2007/0178068 A1 | 8/2007 | Reich et al. |
| 2008/0188437 A1 | 8/2008 | Tolentino et al. |
| 2009/0061487 A1 | 3/2009 | Reich et al. |
| 2009/0104259 A1 | 4/2009 | Tolentino et al. |
| 2010/0168207 A1 | 7/2010 | Tolentino et al. |

FOREIGN PATENT DOCUMENTS

| | | |
|---|---|---|
| EP | 1144623 B1 | 8/2002 |
| EP | 1229134 A2 | 8/2002 |
| EP | 1578933 B1 | 3/2010 |
| IL | 166274 | 9/2010 |
| NZ | 537833 | 12/2010 |
| WO | WO 93/24641 A2 | 12/1993 |
| WO | WO 94/08026 A1 | 4/1994 |
| WO | WO 94/13788 A1 | 6/1994 |
| WO | WO 94/24274 A1 | 10/1994 |
| WO | WO 94/29469 A1 | 12/1994 |
| WO | WO 95/04142 A2 | 2/1995 |
| WO | WO 95/35367 A1 | 12/1995 |
| WO | WO 97/00957 A1 | 1/1997 |
| WO | WO 97/18855 A1 | 5/1997 |
| WO | WO 97/20579 A2 | 6/1997 |
| WO | WO 98/19847 A1 | 5/1998 |
| WO | WO 98/22132 A2 | 5/1998 |
| WO | WO 98/48009 A2 | 10/1998 |
| WO | WO 98/56361 A1 | 12/1998 |
| WO | WO 99/12572 A1 | 3/1999 |
| WO | WO 99/32619 A1 | 7/1999 |
| WO | WO 00/08141 A2 | 2/2000 |
| WO | WO 00/44895 A1 | 8/2000 |
| WO | WO 00/44914 A1 | 8/2000 |
| WO | WO 00/63364 A2 | 10/2000 |
| WO | WO 01/36646 A1 | 5/2001 |
| WO | WO 01/52904 A2 | 7/2001 |
| WO | WO 01/57206 A2 | 8/2001 |
| WO | WO 01/68836 A2 | 9/2001 |
| WO | WO 01/75164 A2 | 10/2001 |
| WO | WO 01/77350 A2 | 10/2001 |
| WO | WO 01/82900 A1 | 11/2001 |
| WO | WO 01/83729 A1 | 11/2001 |
| WO | WO 01/98522 A2 | 12/2001 |
| WO | WO 02/08242 A1 | 1/2002 |
| WO | WO 02/11666 A2 | 2/2002 |
| WO | WO 02/44321 A2 | 6/2002 |
| WO | WO 02/055692 A2 | 7/2002 |
| WO | WO 02/055693 A2 | 7/2002 |
| WO | WO 02/083184 A2 | 10/2002 |
| WO | WO 02/088320 A2 | 11/2002 |
| WO | WO 02/096927 A2 | 12/2002 |
| WO | WO 02/096957 A1 | 12/2002 |
| WO | WO 03/000018 A2 | 1/2003 |
| WO | WO 03/012105 A2 | 2/2003 |
| WO | WO 03/066805 A2 | 8/2003 |
| WO | WO 03/070910 A2 | 8/2003 |
| WO | WO 03/087367 A2 | 10/2003 |
| WO | WO 03/087368 A2 | 10/2003 |
| WO | WO 03/099298 A1 | 12/2003 |
| WO | WO 2004/004769 A1 | 1/2004 |
| WO | WO 2004/013310 A2 | 2/2004 |
| WO | WO 2004/065546 A2 | 8/2004 |
| WO | WO 2004/094606 A2 | 11/2004 |
| WO | WO 2005/028649 A1 | 3/2005 |
| WO | WO 2006/110813 A2 | 10/2006 |
| WO | WO 2007/067981 A2 | 6/2007 |
| WO | WO 2007/146953 A2 | 12/2007 |

(56) References Cited

FOREIGN PATENT DOCUMENTS

| | | |
|---|---|---|
| WO | WO 2008/030996 A2 | 3/2008 |
| WO | WO 2008/110777 A2 | 9/2008 |

OTHER PUBLICATIONS

Adamis, et al., Changes in Retinal Neovascularization after Pegaptanib (Macugen), Therapy in Diabetic Individuals, *Ophthalmology* (Jan. 1, 2006), 113(1):23-28.
Adamis, et al., Inhibition of Vascular Endothelial Growth Factor Prevents Retinal Ischemia-Associated Iris Neovascularization in a Nonhuman Primate, *Arch. Ophthal.* (Jan. 1996), 114(1):66-71.
Addis-Lieser, et al., Opposing Regulatory Roles of Complement Factor 5 in the Development of Bleomycin-Induced Pulmonary Fibrosis, *J. Immunol.* (Aug. 1, 2005), 175(3):1894-1902.
Agami, RNAi and Related Mechanisms and Their Potential Use for Therapy, *Curr. Opin. Chem. Biol.* (Oct. 18, 2002), 6(6):829-834.
Agrawal, et al., Antisense Therapeutics: Is It as Simple as Complementary Base Recognition?, *Mol. Med. Today* (Feb. 1, 2000), 6(2):72-81.
Alexion Pharmaceuticals, Alexion Pharmaceuticals Initiates Treatment in Pivotal Phase III Eculizummab Program in Paraxysmal Nocturnal Emoglobinuria Patients, *News and Information* @ www.alexionpharm.com. (Sep. 23, 2004).
Altschul, et al., Basic Local Alignment Search Tool, *J. Mol. Biol.* (Oct. 5, 1990), 215(3):403-410.
Altschul, et al., Gapped BLAST and PSI-BLAST: a New Generation of Protein Database Search Programs, *Nucleic Acids. Res.* (Sep. 1, 1997), 25(17):3389-3402.
Amarzguioui, Secondary structure prediction and in vitro accessability of mRNA as tools in the selection of target sites for ribozymes, *Nucleic Acids Res.* (Nov. 1, 2000), 28(21):4113-4124.
Ambati, et al., Transscleral Drug Delivery to the Retina and Choroid, *Prog. Retin. Eye Res.* (Mar. 2002), 21(2):145-151.
Ames, et al., Identification of a Selective Nonpeptide Antagonist of the Anaphylatoxin C3a Receptor That Demonstrates Antiinflammatory Activity in Animal Models, *J. Immunol.* (May 15, 2001), 166(10):6341-6348.
Anderson, et al., A Role for Local Inflammation in the Formation of Drusen in the Aging Eye, *Am. J. Ophthalmol.* (Sep. 2002), 134(3):411-431.
Anderson, et al., Vitronectin Gene Expression in the Adult Human Retina, Invest. Ophthalmol. Vis. Sci. (Dec. 1999), 40(13):3305-3315.
Anderson, Human Gene Therapy, *Nature* (Apr. 30, 1998), 392:S25-S31.
Andra, et al., Generation and Characterization of Transgenic Mice Expressing Cobra Venom Factor, *Molecular Immunology* (Oct. 2002), 39(5-6):357-365.
Asahara, et al., Introduction of Gene into the Rabbit Eye by Iontophoresis: Preliminary Report, *JPN J. of Ophthalmol.* (Jan.-Feb. 2001), 45(1):31-39.
Avgeropoulos, et al., New treatment strategies for malignant gliomas, *The Oncologist* (Jun. 1999), 4(3):209-224.
Banan, et al., The Ins and Outs of RNAi in Mammalian Cells, *Curr. Pharm. Biotechnol.* (Oct. 2004), 5(5):441-450.
Banks, et al., Delivery across the blood-brain barrier of antisense directed against Amyloid β: reversal of learning and memory deficits in mice overexpressing Amyloid precursor protein, *J. Pharmaco. Exp. Ther.* (Jun. 1, 2001), 297(3):1113-1121.
Bao, et al., C5a Promotes Development of Experimental Lupus Nephritis which Can be Blocked with a Specific Receptor Antagonist, *Eur. J. Immunol.* (Aug. 2005), 35(8):2496-2506.
Bartz, et al., Production of High-Titer Human Immunodeficiency Virus Type 1 Pseudotyped with Vesiculuar Stomatitis Virus Glycoprotein, *Methods* (Aug. 1, 1997), 12(4):337-342.
Bass, The Short Answer, *Nature* (May 24, 2001), 411:428-429.
Bates, et al., $VEGF_{165}b$, an Inhibitory Splice Variant of Vascular Endothelial Growth Factor, Is Down-Regulated in Renal Cell Carcinoma, *Cancer Res.* (Jul. 15, 2002), 62(14):4123-4131.

Belletti, et al., Modulation of in vivo growth of thyroid tumor-derived cell lines by sense and antisense vascular endothelial growth factor gene, *Oncogene* (Aug. 26, 1999), 18(34):4860-4869.
Bennett, et al., Humoral Response After Administration of E1-deleted Adenoviruses: Immune Privilege of the Subretinal Space, *Hum. Gene Ther.* (Sep. 10, 1996), 7(14):1763-1769 (Abstract).
Berkhout, An Eye-Opener for RNAi Therapeutics, *J. Formos. Med. Assoc.* (Oct. 1, 2008), 107(10):749-750.
Bernstein, et al., Role for a bidentate ribonuclease in the initiation step of RNA interference, *Nature* (Jan. 18, 2001), 409(6818):363-366.
Bernstein, et al., RNA, The Rest is Silence, RNA Society (2001) 7:1509-1521.
Blinder, et al., Effect of Lesion Size, Visual Acuity, and Lesion Composition on Visual Acuity Change with and without Verteporfin Therapy for Choroidal Neovascularization Secondary to Age-Related Macular Degeneration: TAP and VIP Report No. 1, *Am. J. Ophthal.* (Sep. 2003), 136(3):407-418.
Blom, et al., Complement Inhibitor C4b-binding Protein—Friend or Foe in the Innate Immune System?, *Mol. Immunol.* (Apr. 2004), 40(18):1333-1346.
Boado, Antisense drug delivery through the blood-brain barrier, *Adv. Drug Delivery Reviews* (Jul. 1995), 15(1-3):73-107.
Boado, et al., Drug delivery of antisense molecules to the brain for treatment of Alzheimer's disease and cerebral AIDS, *J. Pharm. Sci.* (Nov. 1998), 87(11):1308-1315.
Bok, Evidence for an Inflammatory Process in Age-Related Macular Degeneration Gains New Support, *PNAS USA* (May 17, 2005), 102(20):7053-7054.
Bonilha, et al., Ezrin Promotes Morphogenesis of Apical Microvilli and Basal Infoldings in Retinal Pigment Epithelium, *J. Cell Biol.* (Dec. 27, 1999), 147(7):1533-1548.
Boocock, et al., Expression of Vascular Endothelial Growth Factor and its Receptors flt and KDR in Ovarian Carcinoma, *J. Natl. Cancer Inst.* (Apr. 5, 1995), 8(7):506-516.
Bora, et al., Role of Complement and Complement Membrane Attack Complex in Laser-induced Choroidal Neovascularization, *J. Immun.* (Jan. 1, 2005), 174(1):491-497.
Brantl, Antisense-RNA regulation and RNA Interference, *Biochim. Biophys. Acta* (May 3, 2002), 1575(1-3):15-25.
Bressler, et al., Verteporfin Therapy of Subfoveal Choroidal Neovasculariation in Patients with Age-Related Macular Degeneration, *Arch. Ophthalmol.* (Nov. 2002), 120(11):1443-1454.
Brummelkamp, et al., A System for Stable Expression of Short Interfering RNAs in Mammalian Cells, *Science* (Apr. 19, 2002), 296(5567):550-553.
Bullard, et al., Direct Comparison of Nick-Joining Activity of the Nucleic Acid Ligases from Bacteriophage T4, *Biochem. J.* (Aug. 15, 2006), 398(1):135-144.
Bustin, Absolute Quantification of mRNA Using Real-time Reverse Transcription Polymerase Chain Reaction Assays, *J. Mol. Endocrinol.* (Oct. 2000), 25(2):169-193.
Cai, et al., A Direct Role for C1 Inhibitor in Regulation of Leukocyte Adhesion, *J. Immunol.* (May 15, 2005), 174(10):6462-6466.
Campochiaro, Gene therapy for retinal and choroidal diseases, *Expert Opn. Biol. Ther.* (Jun. 2002), 2(5):537-544.
Capeans, et al., A c-myc Antisense Oligonucleotide Inhibits Human Retinal Pigment Epithelial Cell Proliferation, *Exp. Eye Res.* (May 1998), 66(5):581-589.
Caplen, A New Approach to the Inhibition of Gene Expression, *Biotechnol.* (Feb. 1, 2002), 20(2):49-51.
Caplen, et al., Specific inhibition of gene expression by small double-stranded RNAs in invertebrate and vertebrate systems, *Proc Natl Acad Sci* (Aug. 14, 2001), 98(17):9742-9747.
Caplen, Gene Therapy Progress and Prospect. Downregulating Gene Expression: The Impact of RNA Interference, *Gene Therapy* (Aug. 2004), 11(16):1241-1248.
Caplen, RNAi as a Gene Therapy Approach, *Expert Opin. Biol. Ther.* (Jul. 2003), 3(4):575-586.
Carlson, et al., Perineurium in the *Drosophila* (Diptera: Drosophilidae) Embryo and Its Role in the Blood-Brain/Nerve Barrier, *Int. J. Insect Morphol. Embryol.* (Apr. 1998), 27(2):61-66.

(56) References Cited

OTHER PUBLICATIONS

Chan, et al., Expression of chemokine receptors, CXCR4 and CXCR5, and chemokines, BLC and SDF-1, in the eyes of patients with primary intraocular lymphoma, *Ophthalmology* (Feb. 2003), 110(2):421-426.

Chen, et al., Prevention of Hyperacute Rejection of Pig-to-Monkey Cardiac Xenografts by Chinese Cobra Venom Factor, *Transplant Proc.* (Nov.-Dec. 2001), 33(7-8):3857-3858.

Chirila, et al., The Use of Synthetic Polymers for Delivery of Therapeutic Antisense Oligodeoxynucleotides, *Biomaterials* (Jan. 2002), 23(2):321-342.

Cho, Small Interfering RNA-induced TLR3 Activation Inhibits Blood and Lymphatic Vessel Growth, *PNAS USA* (Apr. 28, 2009), 106(17):7137-7142.

Coburn, et al., siRNAs: a New Wave of RNA-Based Therapeutics, *J. Antimicrob. Chemother.* (Apr. 2003), 51(4):753-756.

Collins, et al., The Human β-Subunit of Rod Photoreceptor cGMP Phosphodiesterase: Complete Retinal cDNA Sequence and Evidence for Expression in Brain, *Genomics* (Jul. 1992), 13(3):698-704.

Conley, et al., Candidate Gene Analysis Suggests a Role for Fatty Acid Biosynthesis and Regulation of the Complement System in the Etiology of Age-Related Maculopathy, *Human Mol. Genetics* (Jul. 15, 2005), 14(14):1991-2002.

Crooke, Progress in Antisense Technology: The End of the Beginning, *Methods Enzymol.* (2000), 313:3-45.

Daiger, Was the Human Genome Project Worth the Effort?, *Science* (Apr. 15, 2005), 308(5720):362-364.

Davis, et al., The Age-Related Eye Disease Study Severity Scale for Age-Related Macular Degeneration: AREDS *Report No. 17, Arch. Ophthalmol.* (Nov. 2005), 123(11):1484-1498.

Deonarain, Ligand-Targeted Receptor-Mediated Vectors for Gene Delivery, *Expert Opin. Ther. Pat.* (Jan. 1998), 8(1):53-69.

Detrick, et al., Inhibition of Human Cytomegalovirus Replication in a Human Retinal Epithelial Cell Model by Antisense Oligonucleotides, *Invest. Ophthalmol. Vis. Sci.* (Jan. 2001), 42(1):163-169.

Devroe, et al., Retrovirus-delivered siRNA, *BMC Biotech.* (Aug. 28, 2002), 2:1-5.

Dornburg, Reticuloendotheliosis Viruses and Derived Vectors, *Gene Therap.* (Jul. 1995), 2(5):301-310.

Dorsett, et al., siRNAs: Applications in Functional Genomics and Potential as Therapeutics, *Nat. Rev. Drug Discov.* (Apr. 2004), 3(4):318-329.

Downward, Science, medicine and the future, RNA Interference, *BMJ* (May 22, 2004), 328(7450):1245-1248.

Dragun, et al., ICAM-1 Antisense Oligodesoxynucleotides Prevent Reperfusion Injury and Enhance Immediate Graft Function in Renal Transplantation, *Kidney Int.* (1998), 54(2):590-602.

Dryja, et al., Mutations in the gene encoding the a subunit of the rod cGMP-gated channel in autosomal recessive retinitis pigmentosa, *PNAS USA* (Oct. 24, 1995), 92(22):10177-10181.

Dyer, et al., The Role of Complement in Immunological Demyelination of the Mammalian Spinal Cord, *Spinal Cord* (Jul. 1, 2005), 43(7):417-425.

Dzitoyeva, et al., Intra-abdominal injection of double stranded RNA into anesthetized adult *Drosophila* triggers RNA interference in the central nervous system, *Mol. Psychiatry* (Nov. 2001), 6(6):665-670.

EBI Accession No. GSN-ADY90830—Retrieved from online database Jun. 16, 2005, VEGF siRNA SEQ ID No. 3868, XP002468091.

EBI Accession No. GSN-ADY90830—Retrieved from online database Jun. 16, 2005, VEGF siRNA SEQ ID No. 3867, XP002468090.

Edwards, et al., Complement Factor H Polymorphism and Age-Related Macular Degeneration, *Science* (Apr. 15, 2005), 308(5720):421-424.

Eglitis, et al., Retroviral Vectors for Introduction of Genes into Mammalian Cells, *BioTechniques* (Jul. 1, 1988), 6(7):608-614.

Elbashir, et al., Analysis of Gene Function in Somatic Mammalian Cells Using Small Interfering RNAs, *Methods* (Feb. 2002), 26(2):199-213.

Elbashir, et al., Duplexes of 21-nucleotide RNAs mediate RNA interference in cultured mammalian cells, *Nature* (May 24, 2001), 411(6836):494-498.

Elbashir, et al., Functional Anatomy of siRNAs for Mediating Efficient RNAi in *Drosophila melanogaster* Embryo Lysate, *EMBO J.* (Dec. 3, 2001), 20(23):6877-6888.

Elbashir, et al., RNA Interference is mediated by 21- and 22-nucleotide RNAs, *Genes Dev.* (Jan. 15, 2001), 15(2):188-200.

Engstrom, et al., Complement C3 is a Risk Factor for the Development of Diabetes: a Population-Based Cohort Study, *Diabetes* (Feb. 2005), 54(2):570-575.

Epstein, Antisense Inhibition of Phosphodiesterase Expression, *Methods* (Jan. 1998), 14(1):21-33.

Erickson, RNAi Revs Up, *Start-Up Emerging Medical Ventures* (Art. #2002900168) (Oct. 1, 2002), pp. 1-12.

Far, et al., The Activity of siRNA in Mammalian Cells is Related to Structural Target Accessiblity: a Comparison with Antisense Oligonucleotides, *Nucleic Acids Res.* (Aug. 1, 2003), 31(15):4417-4424.

Finehout, et al., Complement Protein Isoforms in CSF as Possible Biomarkers for Neurodegenerative Disease, *Dis Markers* (May 16, 2005), 21(2):93-101 (Abstract).

Fire, et al., Potent and Specific Genetic Interference by Double-Stranded RNA in *Caenorhabditis elegans, Nature* (Feb. 19, 1998), 391(6669):806-811.

Fisher, et al., Transduction with Recombinant Adeno-Associated Virus for Gene Therapy is Limited by Leading-Strand Synthesis, *J. Virol.* (Jan. 1996), 70(1):520-532.

Fjose, et al., RNAi and MicroRNAs: from Animal Models to Disease Therapy, *Birth Defects Res.* (Jun. 2006), 78(2):150-171.

Fujita, et al., Complement Activation Accelerates Glomerular Injury in Diabetic Rats, *Nephron* (Feb. 1999), 81(2):208-214.

Fung, et al., Inhibition of Complement, Neutrophil, and Platelet Activation by an Anti-Factor D Monoclonal Antibody in Simulated Cardiopulmonary Bypass Circuits, *J. Thorac. Cardiovasc. Surg.* (Jul. 2001), 122(1):113-122.

Gabizon, et al., Liposome Formulations With Prolonged Circulation Time in Blood and Enhanced Uptake by Tumors, *PNAS USA* (Sep. 1988), 85(18):6949-6953.

Gan, et al., Specific Interference of Gene Function by Double-Stranded RNA in Neuronal Cell Lines, Program No. 772.10, 2001 Neuroscience Meeting Planner. San Diego, CA (Nov. 14, 2001) (Abstract only).

Ganesh, et al., Structure of Vaccinia Complement Protein in Complex with Heparin and Potential Implications for Complement Regulation, *PNAS USA* (Jun. 15, 2004), 101(24):8924-8929.

Gardlik, et al., Vectors and Delivery Systems in Gene Therapy, *Med. Sci. Monit.* (Apr. 2005), 11(4):RA110-121.

Garrett, et al., In vivo use of oligonucleotides to inhibit choroidal neovascularisation in the eye, *J Gene Med* (Jul.-Aug. 2001), 3(4):373-383.

GENBANK Accession No. AF 091352 (1998).
GENBANK Accession No. AF 430806 (2001).
GENBANK Accession No. AJ 010438 (1988).
GENBANK Accession No. AJ 245445, 1999 (Einspanier—Flt1).
GENBANK Accession No. CS 245578 (2005).
GENBANK Accession No. CS 245579 (2005).

Gompels, et al., C1 inhibitor deficiency: consensus document, *Clin Exp. Immunol.* (Mar. 2005), 139(3):379-394.

Goncalves, A concise peer into the background, initial thoughts and practices of human gene therapy, *BioEssays* (May 2005), 27(5):506-517.

Grishok, et al., Genes and Mechanisms Related to RNA Interference Regulate Expression of the Small Temporal RNAs that Control *C. elegans* Development Timing, *Cell* (Jul. 13, 2001), 106:23-34.

Groothuis, The blood-brain and blood-tumor barriers: a review of strategies for increasing drug delivery, *Neuro Oncol.* (Jan. 2000), 2(1):45-59.

Guo, et al., Role of C5A in Inflammatory Responses, *Annu Rev Immunol.* (2005), 23:821-852.

(56) References Cited

OTHER PUBLICATIONS

Hageman, et al., A common haplotype in the complement regulatory gene factor H (HF1/CFH) predisposes individuals to age-related macular degeneration, *Proc Natl Acad Sci USA* (May 17, 2005), 102(20):7227-7232.

Hageman, et al., An Integrated Hypothesis that Considers Drusen as Biomarkers of Immune-Mediated Processes at the RPE-Bruch's Membrane Interface in Aging and Age-Related Macular Degeneration, *Prog Retin Eye Res.* (Nov. 2001), 20(6):705-732.

Hageman, et al., Molecular composition of drusen as related to substructural phenotype, *Mol. Vis.* (Nov. 3, 1999), 5:28-37.

Haines, et al., Complement Factor H Variant Increases the Risk of Age-Related Macular Degeneration, *Science* (Apr. 15, 2005), 308(5720):419-421.

Halstead, et al., Complement Inhibition Abrogates Terminal Injury in Miller Fisher Syndrome, *Ann Neurol.* (Aug. 2005), 58(2):203-210.

Hamilton, et al., A species of small antisense RNA in post-transcriptional gene silencing in plants, *Science* (Oct. 29, 1999), 286(5441): 950-952.

Hammond, et al., Post-transcriptional Gene Silencing by Double-Stranded RNA, *Nat Rev Genet* (Feb. 2001), 2(2):110-119.

Harborth, et al., Self Assembly of NuMA multiarm oligomers as structural units of a nuclear lattice, *EMBO J.* (Mar. 15, 1999), 18(6):1689-1700.

Harborth, et al., Sequence, Chemical, and Structural Variation of Small Interfering RNAs and Short Hairpin RNAs and the Effect on Mammalian Gene Silencing, *Antisense Nucleic Acid Drug Dev.* (Apr. 2003), 13(2):83-105.

Hart, et al., Genotype-Phenotype Correlation of Mouse Pde6b Mutations, *Invest Ophthalmos Vis Sci..* (Sep. 2005), 46(9):3443-3450.

Hart, et al., Initiation of complement activation following oxidative stress. In vitro and in vivo observations, *Mol Immunol.* (Jun. 2004), 41(2-3):165-171.

Hasan, et al., VEGF antagonists, *Expert Opin Biol Ther.* (Jul. 2001), 1(4):703-718.

He, et al., Complement Inhibitors Targeted to the Proximal Tubule Prevent Injury in Experimental Nephrotic Syndrome and Demonstrate a Key Role for C5b-9, *J Immunol.* (May 1, 2005), 174(9):5750-5757.

Hillebrandt, et al., Complement factor 5 is a quantitative trait gene that modifies liver fibrogenesis in mice and humans, *Nat. Genet* (Aug. 2005), 37(8):835-843.

Hodgetts, et al., Complement and myoblast transfer therapy: Donor myoblast survival is enhanced following depletion of host complement C3 using cobra venom factor, but not in the absence of C5, *Immunol Cell Biol.* (Jun. 2001), 79(3):231-239.

Hoeg, et al., In Vitro and In Vivo Efficacy of a HIF-1 Alpha-Antisense Oligonucleotide Containing Locked Nucleic Acids, *ECJ Supplements* (Sep. 24, 2003), pp. S212-S213 (Abstract).

Holash, et al., VEGF-Trap: A VEGF blocker with potent antitumor effects, *Proc Natl Acad Sci USA* (Aug. 20, 2002), 99(17):11393-11398.

Holers, et al., The alternative pathway of complement in disease: opportunities for therapeutic targeting, *Mol Immunol.* (Jun. 2004), 41(2-3):147-152.

Houck, et al., The Vascular Endothelial Growth Factor Family: Identification of a Fourth Molecular Species and Characterization of Alternative Splicing of RNA, *Mol Edocrinol.* (Dec. 1991), 5(12):1806-1814.

Hunt, et al., Vitreous Treatment of Retinal Pigment Epithelial Cells Results in Decreased Expression of FGF-2, *Invest Ophthalmol Vis Sci.* (Oct. 1998), 39(11):2111-2120.

Jakobsdottir, et al., Susceptibility Genes for Age-Related Maculopathy on Chromosome 10q26, *Am J Hum Genet.* (Sep. 2005), 77(3):389-407.

Jen, et al., Suppression of Gene Expression by Targeted Disruption of Messenger RNA: Available Options and Current Strategies, *Stem Cells.* (2000), 18(5):307-319.

Jha, et al., Vaccinia complement control protein: Multi-functional protein and a potential wonder drug, *J Biosci.* (Apr. 2003), 28(3):265-271.

Johnson, et al., A Potential Role for Immune Complex Pathogenesis in Drusen Formation, *Exp Eye Res.* (Apr. 2000), 70(4):441-449.

Johnson, et al., Complement Activation and Inflammatory Processes in Drusen Formation and Age Related Macular Degeneration, *Exp Eye Res.* (Dec. 2001), 73(6):887-896.

Johnson, et al., The Alzheimer's Aβ-peptide is deposited at sites of complement activation in pathologic deposits associated with aging and age-related macular degeneration, *Proc Natl Acad Sci USA* (Sep. 3, 2002), 99(18):11830-11835.

Kang, et al., An Antisense Oligonucleotide that Inhibits the Expression of Hypoxia-Inducible Factor-1 Alpha Alters Hypoxia-Induced Changes in Proliferation and Viability of Human Cardiac Fibroblasts, Abstracts from Scientific Sessions 2001 II-57:274 (Abstract).

Kasschau, et al., A Counterdefensive Strategy of Plant Viruses: Suppression of Posttranscriptional Gene Silencing, *Cell* (Nov. 13, 1998), 95(4):461-470.

Katz, et al., ICAM-1 Antisense Oligodeoxynucleotide Improves Islet Allograft Survival and Function, *Cell Transplant.* (Nov.-Dec. 2000), 9(6):817-828.

Kim, et al., Potent VEGF blockade causes regression of coopted vessels in a model of neuroblastoma, *Proc Natl Acad Sci USA.* (Aug. 20, 2002), 99(17):11399-11404.

Klein, et al., Complement Factor H Polymorphism in Age-Related Macular Degeneration, *Science.* (Apr. 15, 2005), 308(5720):385-389.

Kleinman, et al., Sequence- and target-independent angiogenesis suppression by siRNA via TLR3, *Nature* (Apr. 3, 2008), 452(7187):591-598.

Knight, et al., A Role for the RNase III Enzyme DCR-1 in RNA Interference and Germ Line Development in *Caenorhabditis elegans*, *Science* (Sep. 21, 2001), 293(5538):2269-2271.

Kociok, et al., Upregulation of RAS-GTPase Activating Protein (GAP)-Binding Protein (G3BP), in Proliferating RPE cells, *J Cell Biochem.* (Aug. 1, 1999), 74(2):194-201.

Kociok, et al., Vitreous Treatment of Cultured Human RPE Cells Results in Differential Expression of 10 New Genes, *Invest Ophthalmol Vis Sci.* (Jul. 2002), 43(7):2474-2480.

Kock, et al., Structure and Function of Recombinant Cobra Venom Factor, *J Biol Chem.* (Jul. 16, 2004), 279(29):30836-30843.

Konopatskaya, et al., VEGF$_{165}$b, an endogenous C-terminal splice variant of VEGF, inhibits retinal neovascularization in mice, *Mol Vis.* (May 26, 2006), 12:626-632.

Kostelny, et al., Formation of a Bispecific Antibody by the Use of Leucine Zippers, J Immunol. (Mar. 1, 1992), 148(5):1547-1553.

Krishnamachary, et al., Regulation of Colon Carcinoma Cell Invasion by Hypoxia-Inducible Factor 1, *Cancer Res.* (Mar. 1, 2003), 63(5):1138-1143.

Kuehn, Gene Discovery Provides Clues to Cause of Age-Related Macular Degeneration, *JAMA.* (Apr. 20, 2005), 293(15):1841-1845.

Kurschat, et al., Optimizing splinted ligation of highly structured small RNAs, *RNA.* (Dec. 2005), 11(12):1909-1914.

Lai, et al., The Use of Adenovirus-Mediated Gene Transfer to Develop a Rat Model for Photoreceptor Degeneration, *Invest. Ophthalmol Vis Sci.* (Feb. 2000), 41(2):580-584.

Lawson, et al., Understanding the Glaucoma Gene, *Developmental Control of Gene Expression* (2000), 69-74:14a (Abstract).

Leconte, et al., Impairment of Rod cGMP-Gated Channel α-Subunit Expression Leads to Photoreceptor and Bipolar Cell Degeneration, *Invest. Ophthamol. Vis Sci.* (Mar. 2000), 41(3):917-926.

Lee, et al., Expression of small interfering RNAs targeted against HIV-1 rev transcripts in human cells, *Nat Biotechnol.* (May 2002), 20(5):500-505.

Lee, et al., Imaging Gene Expression in the Brain In Vivo in a Transgenic Mouse Model of Huntington's Disease with an Antisense Radiopharmaceutical and Drug-Targeting Technology, *J Nucl Med.* (Jul. 2002), 43(7):948-956.

Levy, et al., Post-Transcriptional Regulation of Vascular Endothelial Growth Factor by Hypoxia, *J Biol Chem.* (Feb. 2, 1996), 271(5):2746-2753.

(56) References Cited

OTHER PUBLICATIONS

Lewin, et al., Ribozyme rescue of photoreceptor cells in a transgenic rat model of autosomal dominant retinitis pigmentosa, *Nat Med.* (Aug. 1, 1998), 4(8):967-971.

Lewis, et al., A serum-resistant cytofectin for cellular delivery of antisense oligodeoxynucleotides and plasmid DNA, *Proc Natl Acad Sci USA.* (Apr. 16, 1996), 93(8):3176-3181.

Linton, et al., Therapeutic efficacy of a novel membrane-targeted complement regulator in antigen-induced arthritis in the rat, *Arthritis Rheum.* (Nov. 2000), 43(11):2590-2597 (Abstract).

Liu, et al., Ribozyme Knockdown of the γ-Subunit of Rod cGMP Phosphodiesterase Alters the ERG and Retinal Morphology in Wild-Type Mice, *Invest Ophthalmol Vis Sci.* (Oct. 2005), 46(10):3836-3844.

Lu, et al., Delivering siRNA in vivo for Functional Genomics and Novel Therapeutics, *RNA Interference Technology: From Basic Science to Drug Development*, Cambridge Univ. Press (Sep. 1, 2005), 22:303-317.

Lucas, et al., Secreted Immunomodulatory Viral Proteins as Novel Biotherapeutics, *J Immunol.* (Oct. 15, 2004), 173(8):4765-4774.

Manoharan, RNA interference and chemically modified small interfering RNAs, *Curr Opin Chem Biol.* (Dec. 2004), 8(6):570-579.

Marchand, et al., Blockade of in vivo VEGF-mediated angiogenesis by antisense gene therapy: role of Flk-1 and Flt-1 receptors, *Am J Physiol Heart Circ Physiol.* (Jan. 2002), 282(1):H194-H204.

Martinez, et al., Single-Stranded Antisense siRNAs Guide Target RNA Cleavage in RNAi, *Cell* (Sep. 6, 2002), 110(5):563-574.

Mastellos, et al., From atoms to aystems: a cross-disciplinary approach to complement-mediated functions, *Mol Immunol.* (Jun. 2004), 41(2-3):153-164.

Mastellos, et al., Novel biological networks modulated by complement, *Clinical Immunol.* (Jun. 2005), 115(3):225-235.

McCaffrey, et al., RNA interference in adult mice, *Nature.* (Jul. 4, 2002), 418(6893):38-39.

Merriam-Webster's Online Dictionary, Definition of Ligand, http://www.merriam-webster.com/ dictionary/ligand (Jun. 2, 2008).

Miller, Retrovirus Packaging Cells, *Hum Gene Ther.* (Spring 1990), 1(1):5-14 (Abstract).

Miyagishi, et al., U6 promoter-driven siRNAs with four uridine 3' overhangs efficiently suppress target gene expression in mammalian cells, *Nat Biotechnol.* (May 2002), 20(5):497-500.

Miyamoto, et al., Prevention of leukostasis and vascular leakage in streptozotocin-induced diabetic retinopathy via intercellular adhesion molecule-1 inhibition, *Proc Natl Acad Sci USA.* (Sep. 14, 1999), 96(19):10836-10841.

Miyamoto, et al., Vascular Endothelial Growth Factor (VEGF)-Induced Retinal Vascular Permeability is Mediated by Intercellular Adhesion Molecule-1 (ICAM-1), *Am J Pathol.* (May 2000), 156(5):1733-1739.

Mollnes, et al., Complement in inflammatory tissue damage and disease, *Trends Immunol.* (Feb. 2002), 23(2):61-64.

Moromizato, et al., CD18 and ICAM-1 Dependent Corneal Neovascularization and Inflammation after Limbal Injury, *Am J Pathol.* (Oct. 2000), 157(4):1277-1281.

Mothe, et al., Analysis of Green Fluorescent Protein Expression in Transgenic Rats for Tracking Transplanted Neural Stem/Progenitor Cells, *J Histochem Cytochem.* (Oct. 2005), 53(10):1215-1226.

Moulton, Metrics on RNA Secondary Structures, *J Comput Biol.* (Feb.-Apr. 2000), 7(1-2):277-292.

Mullins, et al., Drusen associated with aging and age-related macular degeneration contain proteins common to extracellular deposits associated with atherosclerosis, elastosis, amyloidosis, and dense deposit disease, *FASEB J.* (May 1, 2000), 14(7):835-846.

Nandakumar, et al., RNA Substrate Specificity and Structure-guided Mutational Analysis of Bacteriophage T4 RNA Ligase 2, *J Biol Chem.* (Jul. 23, 2004), 279(30):31337-31347.

Nguyen, et al., Minimising the secondary structure of DNA targets by incorporation of a modified deoxynucleoside: implications for nucleic acid analysis by hybridisation, *Nucleic Acids Res.* (Oct. 15, 2000), 28(20):3904-3909.

Nielsen, Systemic Delivery: The Last Hurdle?, *Gene Ther.* (Jun. 2005), 12(12):956-957.

Nishiwaki, et al., Introduction of short interfering RNA to silence endogenous E-selection in vascular endothelium leads to successful inhibition of leukocyte adhesion, *Biochem Biophys Res Commun.* (Oct. 31, 2003), 310(4):1062-1066.

Novina, et al., siRNA-directed inhibition of HIV-1 infection, *Nat Med.* (Jul. 2002), 8(7):681-686.

Nückel, et al., Alemtuzumab induces enhanced apoptosis in vitro in B-cells from patients with chromic lymphocytic leukemia by antibody-dependent cellular cytotoxicity, *Eur J Pharmacol.* (May 9, 2005), 514(2-3):217-224.

Ogata, et al., Transfection of basic fibroblast growth factor (bFGF) gene or bFGF antisense fene into human fetinal pigment epithelial cells, *Graefe's Arch Clin Exp Ophthalmol.* (Aug. 1999), 237(8):678-684.

Ohali, et al., Complement profile in childhood immune thrombocytopenic purpura: a prospective pilot study, *Ann Hematol.* (Nov. 2005), 84(12):812-815.

Opalinska, et al., Nucleic-Acid Therapeutics: Basic Principles and Recent Applications, Nat Rev Drug Discov. (Jul. 2002), 1(7):503-514.

Ostergaard, et al., Complement activation and diabetic vascular complications, *Clin Chim Acta.* (Nov. 2005), 361(1-2):10-19.

Paddison, et al., Short hairpin RNAs (shRNAs), induce sequence-specific silencing in mammalian cells, *Genes Dev.* (Apr. 15, 2002), 16(8):948-958.

Pardridge, Brain Drug Targeting and Gene Technologies, *Jpn J Pharmacol.* (Oct. 2001), 87(2):97-103.

Pardridge, CNS Drug Design Based on Principles of Blood-Brain Barrier Transport, *J Neurochem.* (May 1998), 70(5):1781-1792.

Pardridge, Drug and gene targeting to the brain with molecular Trojan horses, Nat Rev Drug Discov. (Feb. 2002), 1(2):131-139.

Pardridge, Drug Delivery to the Brain, *J Cereb. Blood Flow Metab.* (Jul. 1997), 17(7):713-731.

Pardridge, et al., Vector-mediated delivery of a polyamide ("peptide"), nucleic acid analogue through the blood-brain barrier in vivo, *Proc Natl Acad Sci USA.* (Jun. 6, 1995), 92(12):5592-5596.

Pardridge, Vector-mediated drug delivery to the brain, *Adv Drug Deliv Rev.* (Apr. 5, 1999), 36(2-3):299-321.

Paroo, et al., Challenges for RNAi in vivo, *Trends Biotechnol.* (Aug. 2004), 22(8):390-394.

Patterson, et al., Cloning and functional analysis of the promoter for KDR/flk-1, a receptor for vascular endothelial growth factor, *J Biol Chem.* (Sep. 29, 1995), 270(39):23111-23118 (Abstract).

Paul, et al., Effective expression of small interfering RNA in human cells, *Nat Biotechnol.* (May 2002), 20(5):505-508.

Peng, et al., Role of C5 in the development of airway inflammation, airway hyperresponsiveness, and ongoing airway response, *J Clin Invest.* (Jun. 2005), 115(6):1590-1600.

Penichet, et al., An Antibody-Avidin Fusion Protein Specific for the Transferrin Receptor Serves as a Delivery Vehicle for Effective Brain Targeting: Initial Applications in Anti-HIV Antisense Drug Delivery to the Brain, *J Immunol.* (Oct. 15, 1999), 163(8):4421-4426.

Philip, et al., Polarized Expression of Monocarboxylate Transporters in Human Retinal Pigment Epithelium and ARPE-19 Cells, *Invest Ophthalmol Vis Sci.* (Apr. 1, 2003), 44(4):1716-1721.

Pineda, et al., The genetic network of prototypic planarian eye regeneration is Pax6 independent, *Development.* (Mar. 2002), 129(6):1423-1434.

Pratt, et al., Nontransgenic Hyperexpression of a Complement Regulator in Donor Kidney Modulates Transplant Ischemia/Reperfusion Damage, Acute Rejection, and Chronic Nephropathy, *Am J Pathol.* (Oct. 2003), 163(4):1457-1465.

Qian, et al., Targeted Drug Delivery via the Transferrin Receptor-Mediated Endocytosis Pathway, *Pharmacol Rev.* (Dec. 2002), 54(4):561-587.

Ramon, et al., Molecular Biology of Retinitis Pigmentosa: Therapeutic Implications, *Current Pharma.* (Dec. 2004), 2(4):339-349.

Reich, et al., Small Interfering RNA (siRNA), targeting VEGF Effectively Inhibits Ocular Neovascularization in a Mouse Model, *Mol. Vis.* (May 30, 2003), 9(31):210-216.

(56) References Cited

OTHER PUBLICATIONS

Remington's *Pharmaceutical Sciences*, 17th ed., Mack Publishing Co., Easton, PA. (1985).
Rennel, et al., Recombinant human $VEGF_{165}b$ Protein is an effective anti-cancer agent in mice, *Eur J Cancer* (Sep. 2008), 44(13):1883-1894.
Rennel, et al., The endogenous anti-angiogenic VEGF isoform, $VEGF_{165}b$ inhibits human tumour growth in mice, *Br J Cancer* (Apr. 8, 2008), 98(7):1250-1257.
Roberts, et al., Efficient expression of ribozyme and reduction of stromelysin mRNA in cultured cells and tissue from rabbit knee via Adeno-associated Virus (AAV), *Gene Therapy and Mol. Biol.* (Dec. 1999), 4:45-58.
Rosenfeld, et al., Maximum Tolerated Dose of a Humanized Anti-Vascular Endothelial Growth Factor Antibody Fragment for Treating Neovascular Age-Related Macular Degeneration, *Opthalmology*. (Jun. 2005), 112(6):1048-1053.
Rother, et al., Inhibition of terminal complement: a novel therapeutic approach for the treatment of systemic lupus erythematosus, *Lupus* (2004), 13(5):328-334.
Rubinson, et al., A lentivirus-based system to functionally silence genes in primary mammalian cells, stem cells and transgenic mice by RNA interference, *Nat Genet*. (Mar. 2003), 33(3):401-406 (Abstract).
Rummelt, et al., Triple retinal infection with human immunodeficiency virus type 1, cytomegalovirus, and herpes simplex virus type 1. Light and electron microscopy, immunohistochemistry, and in situ hybridization, *Ophalmology*. (Feb. 1994), 101(2):270-279 (Abstract Only).
Russell, et al., Location, Substructure, and Composition of Basal Laminar Drusen Compared with Drusen Associated with Aging and Age-Related Macular Degeneration, *Am J Ophthalmol*. (Feb. 2000), 129(2):205-214.
Sakurai, et al., Targeted Disruption of the CD18 or ICAM-1 Gene Inhibits Choroidal Neovascularization, *Invest Ophthalmol Vis Sci*. (Jun. 2003), 44(6):2743-2749.
Samarsky, et al., RNAi in drug development: Practical Considerations, RNA Interference Tech., Cambridge (Appasani ed.), (Sep. 1, 2005), pp. 384-395.
Samulski, et al., A Recombinant Plasmid from Which an Infectious Adeno-Associated Virus Genome Can Be Excised in Vitro and its use to Study Viral Replication, *J Virol*. (Oct. 1987), 61(10):3096-3101.
Samulski, et al., Helper-Free Stocks of Recombinant Adeno-Associated Viruses: Normal Integration Does Not Require Viral Gene Expression, *J Virol*. (Sep. 1989), 63(9):3822-3828.
Sato, et al., Human cDNA for Vascular Endothelial Growth Factor Isoform VEGF121, GenBank Accession No. AF214570. (Sep. 1999) (see Genbank).
Scanlon, Anti-Genes: siRNA, Ribozymes and Antisense, *Curr Pharm Biotechnol*. (Oct. 2004), 5(5):415-420.
Schroder, et al., A single-stranded promoter for RNA polymerase III, *Proc Natl Acad Sci USA*. (Feb. 4, 2003), 100(3):934-939.
Sewell, et al., Complement C3 and C5 play critical roles in traumatic brain cryoinjury: blocking effects on neutrophil extravasation by C5a receptor antagonist, *J Neuroimmunol*. (Oct. 2004), 155(1-2):55-63.
Shen, et al., A Study of Cobra Venom Factor in Ex Vivo Pig Liver Perfusion Model, *Transplantation Proc*. (Nov.-Dec. 2001), 33(7-8):3860-3861.
Shen, et al., Suppression of ocular neovascularization with siRNA targeting VEGF receptor 1, *Gene Ther*. (Feb. 2006), 13(3):225-234.
Shi, et al., Antisense imaging of gene expression in the brain in vivo, *Proc Natl Acad Sci USA*. (Dec. 19, 2000), 97(26):14709-14714.
Shi, et al., Inhibition of renal cell carcinoma antiogenesis and growth by antisense oligonucleotides targeting vascular endothelial growth factor, *Br J Cancer* (Jul. 1, 2002), 87(1):119-126.
Shibuya, et al., Nucleotide sequence and expression of a novel human receptor-type tyrosine kinaase gene (flt), closely related to the this family, *Oncogene*. (Apr. 1990), 5(4):519-524 (Abstract).

Shim, et al., Inhibition of Angiopoietin-1 Expression in Tumor Cells by an Antisense RNA Approach Inhibited Xenograft Tumor Growth in Immunodeficient Mice, *Int J Cancer*. (Oct. 1, 2001), 94(1):6-15.
Shoji, et al., Current Status of Delivery Systems to Improve Target Efficacy of Oligonucleotides, *Curr Pharm Des*. (2004), 10(7):785-796.
Shu, et al., Sphingosine Kinase Mediates Vascular Endothelial Growth Factor-Induced Activation of Ras and Mitogen-Activated Protein Kinases, *Mol Cell Biol*. (Nov. 2002), 22(22):7758-7768.
Simeoni, et al., Peptide-Based Strategy for siRNA Delivery into Mammalian Cells, *Methods Mol. Biol*. (2005), 309:251-260.
Sioud, siRNA Delivery in Vivo, *Methods Mol Biol*. (2005), 309:237-249.
Smith, et al., Membrane-targeted complement inhibitors, *Mol Immunol*. (Aug. 2001), 38(2-3):249-255.
Smith, et al., Rational selection of antisense oligonucleotide sequences, *Eur J Pharm Sci*. (Sep. 2000), 11(3):191-198.
Sohail, et al., Selecting optimal antisense reagents, *Adv Drug Deliv Rev*. (Oct. 31, 2000), 44(1):23-34.
Sohn, et al., Chronic Low Level Complement Activation within the Eye is Controlled by Intraocular Complement Regulatory Proteins, *Invest Ophthalmol Vis Sci*. (Oct. 2000), 41(11):3492-3502.
Sohn, et al., Complement Regulatory Activity of Normal Human Intraocular Fluid is Mediated by MCP, DAF and CD59, *Invest Ophthalmol Vis Sci*. (Dec. 2000), 41(13):4195-4202.
Sohn, et al., Tolerance is dependent on complement C3 fragment iC3b binding to antigen-presenting Cells, *Nat Med*. (Feb. 2003), 9(2):206-212.
Songsivilai, et al., Bispecific antibody: a tool for diagnosis and treatment of disease, *Clin Exp Immunol*. (Mar. 1990), 79(3):315-321.
Spaide, et al., Intravitreal Bevacizumab Treatment of Choroidal Neovascularization Secondary to Age-Related Macular Degeneration, *Retina* (2006), 26(4):383-390.
Speidl, et al., Complement component C5a predicts future cardiovascular events in patients with advanced atherosclerosis, *Eur Heart J*. (Nov. 2005), 26(21):2294-2299.
Speirs, et al., Production of VEGF and expression of the VEGF receptors Flt-1 and KDR in primary cultures of epithelial and stromal cells derived from breast tumours, *Br J Cancer* (May 1999), 80(5-6):898-903.
Stein, et al., Oligodeoxynucleotides as Inhibitors of Gene Expression: A Review, *Cancer Res*. (May 15, 1988), 48(10):2659-2668.
Strachan, et al., A New Small Molecule C5a Receptor Antagonist Inhibits the Reverse-Passive Arthus Reaction and Endotoxic Shock in Rats, *J Immunol*. (Jun. 15, 2000), 164(12):6560-6565.
Sun, et al., Gene transfer of antisense hypoxia inducible factor-1 α enhances the therapeutic efficacy of cancer immunotherapy, *Gene Ther*. (Apr. 2001), 8(8):638-645.
Sun, et al., Prolonged cardiac xenograft survival in guinea pig-to-rat model by a highly active cobra venom factor, *Toxicon*. (Sep. 1, 2003), 42(3):257-262.
Szoka, Jr., et al., Comparative Properties and Methods of Preparation of Lipid Vesicles (Liposomes), *Ann Rev Biophys Bioeng*. (Jun. 1980), 9:467-508.
Thurman, et al., A novel inhibitor of the alternative complement pathway prevents antiphospholipid antibody-induced pregnancy loss in mice, *Mol Immunol*. (Jan. 2005), 42(1):87-97.
Tischer, et al., The Human Gene for Vascular Endothelial Growth Factor. Multiple Protein Forms Are Encoded Through Alternative Exon Splicing, J Biol Chem. (Jun. 25, 1991), 266(18):11947-11954 (Abstract).
Tolentino, et al., Intravitreal Injection of Vascular Endothelial Growth Factor Small Interfering RNA Inhibits Growth and Leakage in a Nonhuman Primate, Laser-induced Model of Choroidal Neovascularization, *Retina*. (Feb. 2004), 24(1):132-138.
Toschi, Influence of mRNA Self-Structure on Hybridization: Computational Tools for Antisense Sequence Selection, *Methods* (Nov. 2000), 22(3):261-269.
Trudeau, et al., An Intersubunit Interaction Regulates Trafficking of Rod Cyclic Nucleotide-Gated Channels and Is Disrupted in an Inherited Form of Blindness, *Neuron*. (Apr. 11, 2002), 34(2):197-207.
Tuschl, Expanding small RNA interference, *Nat Biotechnol*. (May 2002), 20(5):446-448.

(56) References Cited

OTHER PUBLICATIONS

Tuschl, The siRNA user guide, http://www.mpidpc.gwdg.de/abteilungen/100/105/sirna.html (May 6, 2004).
Tuschl, The siRNA user guide, http://www.mpidpc.gwdg.de/abteilungen/100/105/sirna.html (Oct. 11, 2002).
Tyler, et al., Peptide nucleic acids targeted to the neurotensin receptor and administered i.p. cross the blood-brain barrier and specifically reduce gene expression, *Proc Natl Acad Sci USA*. (Jun. 8, 1999), 96(12):7053-7058.
Van Brunt, Shoot the Messenger, Signals Magazine, http://www.signalsmag.com/signalsmag/3DF5AEF6049CC81C99256C1D0055BAA, (Aug. 22, 2002).
Van Der Krol, et al., Modulation of Eukaryotic Gene Expression by Complementary RNA or DNA Sequences, *BioTechniques*. (Nov.-Dec. 1988), 6(10):958-976.
Verma, et al., Gene therapy—promises, problems and prospects, *Nature*. (Sep. 18, 1997), 389(6648):239-242.
Verma, et al., Gene Therapy: Twenty-First Century Medicine, *Annu Rev Biochem*. (2005), 74:711-738.
Vickers, et al., Efficient Reduction of Target RNAs by Small Interfering RNA and RNase H-dependent Antisense Agents, *J Biol Chem*. (Feb. 28, 2003), 278(9):7108-7118.
Vogel, et al., Recombinant cobra venom factor, *Mol Immunol*. (Jun. 2004), 41(2-3):191-199.
Walport, Complement at the Interface Between Innate and Adaptive Immunity, Complement, First of Two Parts, *N Engl J Med*. (Apr. 12, 2001), 344(14):1058-1066.
Walport, Complement at the Interface Between Innate and Adaptive Immunity, Complement: Second of Two Parts, *N Engl J Med*. (Apr. 12, 2001), 344(15):1140-1144.
Ward, et al., Genomic structure of the human angiopoietins show polymorphism in angiopoietin-2, *Cytogenet Cell Genet*. (2001), 94(3-4):147-154.
Warren, et al., Successful ICAM-1 Gene Inactivation in Pluripotent Stem Cell using RNA Interference and in Situ Expressed Antisense/Ribozyme Transgenes, *J Am Soc Nephrology* (2002), p. 101A (Abstract).
Weber, et al., Genomic organization and complete sequence of the human gene encoding the β-subunit of the cGMP phosphodiesterase and its localisation to 4p16.3, *Nucleic Acids Res*. (Nov. 25, 1991), 19(22):6263-6268.
Wu, et al., Pharmacokinetics and Blood-Brain Barrier Transport of [$^3$H]-Biotinylated Phosphorothioate Oligodeaoxynucleotide Conjugated to a Vector-Mediated Drug Delivery System, *J Pharmacol Exp Ther*. (Jan. 1996), 276(1):206-211.
Xia, et al., siRNA-mediated gene silencing in vitro and in vivo, *Nat Biotechnol*. (Oct. 2002), 20(10):1006-1010.
Xu, et al., Protective effect of membrane cofactor protein against complement-dependent injury, *Acta Pharmacol Sin*. (Aug. 2005), 26(8):987-991.
Zamore, et al., RNAi: double-stranded RNA directs the ATP-dependent cleavage of mRNA at 21 to 23 nucleotide intervals, *Cell* (Mar. 31, 2000), 101:25-33.
Zareparsi, et al., Strong Association of the Y402H Variant in Complement Factor H at 1q32 with Susceptibility to Age-Related Macular Degeneration, *Am J Hum Genet*. (Jul. 2005), 77(1):149-153.
Zheng, et al., Protection of Renal Ischemia Injury Using Combination Gene Silencing of Complement 3 and Caspase 3 Genes, *Transplantation* (Dec. 27, 2006), 82(12):1781-1786.

* cited by examiner

COMPOSITIONS AND METHODS FOR SIRNA INHIBITION OF ANGIOGENESIS

CROSS REFERENCE TO RELATED APPLICATION

This application is a continuation of U.S. application Ser. No. 11/422,982, filed Jun. 8, 2006, now U.S. Pat. No. 8,546,345, which is a divisional of U.S. application Ser. No. 10/294,228 filed on Nov. 14, 2002, now U.S. Pat. No. 7,148,342, which claims the benefit of U.S. provisional patent application Ser. No. 60/398,417, filed on Jul. 24, 2002, all of which are incorporated herein by reference in their entireties.

REFERENCE TO GOVERNMENT GRANT

The invention described herein was supported in part by NIH/NEI grant no. R01-EY10820, EY-13410 and EY12156. The U.S. government has certain rights in this invention.

JOINT RESEARCH AGREEMENT

NOT APPLICABLE

FIELD OF THE INVENTION

This invention relates to the regulation of gene expression by small interfering RNA, in particular for treating diseases or conditions involving angiogenesis.

BACKGROUND OF THE INVENTION

Angiogenesis, defined as the growth of new capillary blood vessels or "neovascularization," plays a fundamental role in growth and development. In mature humans, the ability to initiate angiogenesis is present in all tissues, but is held under strict control. A key regulator of angiogenesis is vascular endothelial growth factor ("VEGF"), also called vascular permeability factor ("VPF"). VEGF exists in at least four different alternative splice forms in humans ($VEGF_{121}$, $VEGF_{165}$, $VEGF_{189}$ and $VEGF_{206}$), all of which exert similar biological activities.

Angiogenesis is initiated when secreted VEGF binds to the Flt-1 and Flk-1/KDR receptors (also called VEGF receptor 1 and VEGF receptor 2), which are expressed on the surface of endothelial cells. Flt-1 and Flk-1/KDR are transmembrane protein tyrosine kinases, and binding of VEGF initiates a cell signal cascade resulting in the ultimate neovascularization in the surrounding tissue.

Aberrant angiogenesis, or the pathogenic growth of new blood vessels, is implicated in a number of conditions. Among these conditions are diabetic retinopathy, psoriasis, exudative or "wet" age-related macular degeneration ("ARMD"), rheumatoid arthritis and other inflammatory diseases, and most cancers. The diseased tissues or tumors associated with these conditions express abnormally high levels of VEGF, and show a high degree of vascularization or vascular permeability.

ARMD in particular is a clinically important angiogenic disease. This condition is characterized by choroidal neovascularization in one or both eyes in aging individuals, and is the major cause of blindness in industrialized countries.

A number of therapeutic strategies exist for inhibiting aberrant angiogenesis, which attempt to reduce the production or effect of VEGF. For example, anti-VEGF or anti-VEGF receptor antibodies (Kim E S et al. (2002), *PNAS USA* 99: 11399-11404), and soluble VEGF "traps" which compete with endothelial cell receptors for VEGF binding (Holash J et al. (2002), *PNAS USA* 99: 11393-11398) have been developed. Classical VEGF "antisense" or aptamer therapies directed against VEGF gene expression have also been proposed (U.S. published application 2001/0021772 of Uhlmann et al.). However, the anti-angiogenic agents used in these therapies can produce only a stoichiometric reduction in VEGF or VEGF receptor, and the agents are typically overwhelmed by the abnormally high production of VEGF by the diseased tissue. The results achieved with available anti-angiogenic therapies have therefore been unsatisfactory.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), *Nature* 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), *Genes Dev,* 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Elbashir S M et al. (2001), supra, has shown that synthetic siRNA of 21 and 22 nucleotides in length, and which have short 3' overhangs, are able to induce RNAi of target mRNA in a Drosophila cell lysate. Cultured mammalian cells also exhibit RNAi degradation with synthetic siRNA (Elbashir S M et al. (2001) *Nature,* 411: 494-498), and RNAi degradation induced by synthetic siRNA has recently been shown in living mice (McCaffrey A P et al. (2002), *Nature,* 418: 38-39; Xia H et al. (2002), *Nat. Biotech.* 20: 1006-1010). The therapeutic potential of siRNA-induced RNAi degradation has been demonstrated in several recent in vitro studies, including the siRNA-directed inhibition of HIV-1 infection (Novina C D et al. (2002), *Nat. Med.* 8: 681-686) and reduction of neurotoxic polyglutamine disease protein expression (Xia H et al. (2002), supra).

What is needed, therefore, are agents which selectively inhibit expression of VEGF or VEGF receptors in catalytic or sub-stoichiometric amounts.

SUMMARY OF THE INVENTION

The present invention is directed to siRNAs which specifically target and cause RNAi-induced degradation of mRNA from VEGF, Flt-1 and Flk-1/KDR genes. The siRNA compounds and compositions of the invention are used to inhibit angiogenesis, in particular for the treatment of cancerous tumors, age-related macular degeneration, and other angiogenic diseases.

Thus, the invention provides an isolated siRNA which targets human VEGF mRNA, human Flt-1 mRNA, human Flk-1/KDR mRNA, or an alternative splice form, mutant or cognate thereof. The siRNA comprises a sense RNA strand and an antisense RNA strand which form an RNA duplex. The sense RNA strand comprises a nucleotide sequence identical to a target sequence of about 19 to about 25 contiguous nucleotides in the target mRNA.

The invention also provides recombinant plasmids and viral vectors which express the siRNA of the invention, as well as pharmaceutical compositions comprising the siRNA of the invention and a pharmaceutically acceptable carrier.

The invention further provides a method of inhibiting expression of human VEGF mRNA, human Flt-1 mRNA, human Flk-1/KDR mRNA, or an alternative splice form, mutant or cognate thereof, comprising administering to a subject an effective amount of the siRNA of the invention such that the target mRNA is degraded.

The invention further provides a method of inhibiting angiogenesis in a subject, comprising administering to a subject an effective amount of an siRNA targeted to human VEGF mRNA, human Flt-1 mRNA, human Flk-1/KDR mRNA, or an alternative splice form, mutant or cognate thereof.

The invention further provides a method of treating an angiogenic disease, comprising administering to a subject in need of such treatment an effective amount of an siRNA targeted to human VEGF mRNA, human Flt-1 mRNA, human Flk-1/KDR mRNA, or an alternative splice form, mutant or cognate thereof, such that angiogenesis associated with the angiogenic disease is inhibited.

DETAILED DESCRIPTION OF THE INVENTION

Figure 1A:
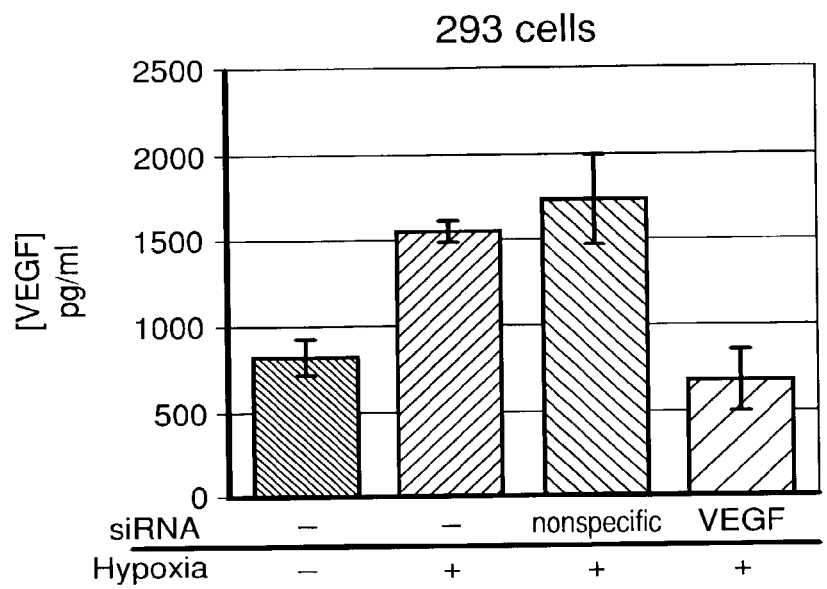
FIGS. 1A and 1B are a histograms of VEGF concentration (in pg/ml) in hypoxic 293 and HeLa cells treated with no siRNA ("−"); nonspecific siRNA ("nonspecific"); or siRNA targeting human VEGF mRNA ("VEGF"). VEGF concentration (in pg/ml) in non-hypoxic 293 and HeLa cells is also shown. Each bar represents the average of four experiments, and the error is the standard deviation of the mean.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to VEGF, Flt-1 or Flk-1/KDR mRNA are advantageously used to inhibit angiogenesis, in particular for the treatment of angiogenic disease. The siRNA of the invention are believed to cause the RNAi-mediated degradation of these mRNAs, so that the protein product of the VEGF, Flt-1 or Flk-1/KDR genes is not produced or is produced in reduced amounts. Because VEGF binding to the Flt-1 or Flk-1/KDR receptors is required for initiating and maintaining angiogenesis, the siRNA-mediated degradation of VEGF, Flt-1 or Flk-1/KDR mRNA inhibits the angiogenic process.

The invention therefore provides isolated siRNA comprising short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is identical to a target sequence contained within the target mRNA.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules (see Tuschl, T. (2002), supra).

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

As used herein, "target mRNA" means human VEGF, Flt-1 or Flk-1/KDR mRNA, mutant or alternative splice forms of human VEGF, Flt-1 or Flk-1/KDR mRNA, or mRNA from cognate VEGF, Flt-1 or Flk-1/KDR genes.

As used herein, a gene or mRNA which is "cognate" to human VEGF, Flt-1 or Flk-1/KDR is a gene or mRNA from another mammalian species which is homologous to human VEGF, Flt-1 or Flk-1/KDR. For example, the cognate VEGF mRNA from the mouse is given in SEQ ID NO: 1.

Splice variants of human VEGF are known, including $VEGF_{121}$ (SEQ ID NO: 2), $VEGF_{165}$ (SEQ ID NO: 3), $VEGF_{189}$ (SEQ ID NO: 4) and $VEGF_{206}$ (SEQ ID NO: 5). The mRNA transcribed from the human VEGF, Flt-1 (SEQ ID NO: 6) or Flk-1/KDR (SEQ ID NO: 7) genes can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), J. Mol. Endocrinol. 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the VEGF, Flt-1 or Flk-1/KDR genes can be used to query such a database to determine whether ESTs representing alternatively spliced mRNAs have been found for a these genes.

A technique called "RNAse protection" can also be used to identify alternatively spliced VEGF, Flt-1 or Flk-1/KDR mRNAs. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced VEGF, Flt-1 or Flk-1/KDR mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

mRNA produced from mutant VEGF, Flt-1 or Flk-1/KDR genes can also be readily identified through the techniques described above for identifying alternative splice forms. As used herein, "mutant" VEGF, Flt-1 or Flk-1/KDR genes or mRNA include human VEGF, Flt-1 or Flk-1/KDR genes or mRNA which differ in sequence from the VEGF, Flt-1 or Flk-1/KDR sequences set forth herein. Thus, allelic forms of these genes, and the mRNA produced from them, are considered "mutants" for purposes of this invention.

It is understood that human VEGF, Flt-1 or Flk-1/KDR mRNA may contain target sequences in common with their respective alternative splice forms, cognates or mutants. A single siRNA comprising such a common targeting sequence can therefore induce RNAi-mediated degradation of different RNA types which contain the common targeting sequence.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention can also comprise a 3' overhang. As used herein, a "3' overhang" refers to at least one unpaired nucleotide extending from the 3'-end of a duplexed RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA of the invention comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon (see, e.g., the target sequences of SEQ ID NOS: 73 and 74 in Table 1 below, which are within 100 nt of the 5'-end of the $VEGF_{121}$ cDNA For example, a suitable target sequence in the $VEGF_{121}$ cDNA sequence is:

```
                              (SEQ ID NO: 8)
        TCATCACGAAGTGGTGAAG
```

Thus, an siRNA of the invention targeting this sequence, and which has 3' uu overhangs on each strand (overhangs shown in bold), is:

```
                                  (SEQ ID NO: 9)
        5'-ucaucacgaaguggugaaguu-3'

(SEQ ID NO: 10)
        3'-uuaguagugcuucaccacuuc-5'
```

An siRNA of the invention targeting this same sequence, but having 3' TT overhangs on each strand (overhangs shown in bold) is:

```
                                  (SEQ ID NO: 11)
        5'-ucaucacgaaguggugaagTT-3'

(SEQ ID NO: 12)
        3'-TTaguagugcuucaccacuuc-5'
```

Other $VEGF_{121}$ target sequences from which siRNA of the invention can be derived are given in Table 1. It is understood that all $VEGF_{121}$ target sequences listed in Table 1 are within that portion of the $VEGF_{121}$ alternative splice form which is common to all human VEGF alternative splice forms. Thus, the $VEGF_{121}$ target sequences in Table 1 can also target $VEGF_{165}$, $VEGF_{189}$ and $VEGF_{206}$ mRNA. Target sequences which target a specific VEGF isoform can also be readily identified. For example, a target sequence which targets $VEGF_{165}$ mRNA but not $VEGF_{121}$ mRNA is AACGTACTTGCAGATGTGACA (SEQ ID NO: 13).

TABLE 1

VEGF Target Sequences

| target sequence | SEQ ID NO: |
|---|---|
| GTTCATGGATGTCTATCAG | 14 |
| TCGAGACCCTGGTGGACAT | 15 |
| TGACGAGGGCCTGGAGTGT | 16 |
| TGACGAGGGCCTGGAGTGT | 17 |
| CATCACCATGCAGATTATG | 18 |
| ACCTCACCAAGGCCAGCAC | 19 |
| GGCCAGCACATAGGAGAGA | 20 |
| CAAATGTGAATGCAGACCA | 21 |
| ATGTGAATGCAGACCAAAG | 22 |
| TGCAGACCAAAGAAAGATA | 23 |
| AGAAAGATAGAGCAAGACA | 24 |
| GAAAGATAGAGCAAGACAA | 25 |
| GATAGAGCAAGACAAGAAA | 26 |
| GACAAGAAAATCCCTGTGG | 27 |

TABLE 1-continued

VEGF Target Sequences

| target sequence | SEQ ID NO: |
|---|---|
| GAAAATCCCTGTGGGCCTT | 28 |
| AATCCCTGTGGGCCTTGCT | 29 |
| TCCCTGTGGGCCTTGCTCA | 30 |
| GCATTTGTTTGTACAAGAT | 31 |
| GATCCGCAGACGTGTAAAT | 32 |
| ATGTTCCTGCAAAAACACA | 33 |
| TGTTCCTGCAAAAACACAG | 34 |
| AAACACAGACTCGCGTTGC | 35 |
| AACACAGACTCGCGTTGCA | 36 |
| ACACAGACTCGCGTTGCAA | 37 |
| CACAGACTCGCGTTGCAAG | 38 |
| GGCGAGGCAGCTTGAGTTA | 39 |
| ACGAACGTACTTGCAGATG | 40 |
| CGAACGTACTTGCAGATGT | 41 |
| CGTACTTGCAGATGTGACA | 42 |
| GTGGTCCCAGGCTGCACCC | 43 |
| GGAGGAGGGCAGAATCATC | 44 |
| GTGGTGAAGTTCATGGATG | 45 |
| AATCATCACGAAGTGGTGAAG | 46 |
| AAGTTCATGGATGTCTATCAG | 47 |
| AATCGAGACCCTGGTGGACAT | 48 |
| AATGACGAGGGCCTGGAGTGT | 49 |
| AACATCACCATGCAGATTATG | 50 |
| AAACCTCACCAAGGCCAGCAC | 51 |
| AAGGCCAGCACATAGGAGAGA | 52 |
| AACAAATGTGAATGCAGACCA | 53 |
| AAATGTGAATGCAGACCAAAG | 54 |
| AATGCAGACCAAAGAAAGATA | 55 |
| AAAGAAAGATAGAGCAAGACA | 56 |
| AAGAAAGATAGAGCAAGACAA | 57 |
| AAGATAGAGCAAGACAAGAAAAT | 58 |
| AAGACAAGAAAATCCCTGTGGGC | 59 |
| AAGAAAATCCCTGTGGGCCTTGC | 60 |
| AATCCCTGTGGGCCTTGCTCAGA | 61 |
| AAGCATTTGTTTGTACAAGATCC | 62 |
| AAGATCCGCAGACGTGTAAATGT | 63 |
| AAATGTTCCTGCAAAAACACAGA | 64 |

TABLE 1-continued

VEGF Target Sequences

| target sequence | SEQ ID NO: |
|---|---|
| AATGTTCCTGCAAAAACACAGAC | 65 |
| AAAAACACAGACTCGCGTTGCAA | 66 |
| AAAACACAGACTCGCGTTGCAAG | 67 |
| AAACACAGACTCGCGTTGCAAGG | 68 |
| AACACAGACTCGCGTTGCAAGGC | 69 |
| AAGGCGAGGCAGCTTGAGTTAAA | 70 |
| AAACGAACGTACTTGCAGATGTG | 71 |
| AACGAACGTACTTGCAGATGTGA | 72 |
| AAGTGGTCCCAGGCTGCACCCAT | 73 |
| AAGGAGGAGGGCAGAATCATCAC | 74 |
| AAGTGGTGAAGTTCATGGATGTC | 75 |
| AAAATCCCTGTGGGCCTTGCTCA | 76 |
| GGCAGAATCATCACGAAGTGG | 81 |
| CCTGGTGGACATCTTCCAGGA | 82 |
| GAGATCGAGTACATCTTCAAG | 83 |
| TGGAGTGTGTGCCCACTGAGG | 84 |
| GAGCTTCCTACAGCACAACAA | 85 |
| TTGCTCAGAGCGGAGAAAGCA | 86 |
| CACACACTCGCGTTGCAAGGC | 87 |
| TCACCATGCAGATTATGCGGA | 88 |
| TAGAGCAAGACAAGAAAATCC | 89 |
| CCGCAGACGTGTAAATGTTCC | 90 |

The siRNA of the invention can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol,* 20: 446-448; Brummelkamp T R et al. (2002), *Science* 296: 550-553; Miyagishi M et al. (2002), *Nat. Biotechnol.* 20: 497-500; Paddison P J et al. (2002), *Genes Dev.* 16: 948-958; Lee N S et al. (2002), *Nat. Biotechnol.* 20: 500-505; and Paul C P et al. (2002), *Nat. Biotechnol.* 20: 505-508, the entire disclosures of which are herein incorporated by reference.

A plasmid comprising nucleic acid sequences for expressing an siRNA of the invention is described in Example 7 below. That plasmid, called pAAVsiRNA, comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA of the invention.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA of the invention can also be expressed from recombinant viral vectors intracellularly at or near the area of neovascularization in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from AV and AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA of the invention, a method for constructing the recombinant AV vector, and a method for delivering the vector into target cells, are described in Xia H et al. (2002), *Nat. Biotech.* 20: 1006-1010.

Suitable AAV vectors for expressing the siRNA of the invention, methods for constructing the recombinant AAV vector, and methods for delivering the vectors into target cells are described in Samulski R et al. (1987), *J. Virol.* 61: 3096-3101; Fisher K J et al. (1996), *J. Virol.,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. An exemplary method for generating a recombinant AAV vector of the invention is described in Example 7 below.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of VEGF, Flt-1 or Flk-1/KDR receptor protein in the cultured cells can be measured by ELISA or Western blot. A suitable cell culture system for measuring the effect of the present siRNA on target mRNA or protein levels is described in Example 1 below.

RNAi-mediated degradation of target mRNA by an siRNA containing a given target sequence can also be evaluated with animal models of neovascularization, such as the ROP or CNV mouse models. For example, areas of neovascularization in an ROP or CNV mouse can be measured before and after administration of an siRNA. A reduction in the areas of neovascularization in these models upon administration of the siRNA indicates the down-regulation of the target mRNA (see Example 6 below).

As discussed above, the siRNA of the invention target and cause the RNAi-mediated degradation of VEGF, Flt-1 or Flk-1/KDR mRNA, or alternative splice forms, mutants or cognates thereof. Degradation of the target mRNA by the present siRNA reduces the production of a functional gene product from the VEGF, Flt-1 or Flk-1/KDR genes. Thus, the invention provides a method of inhibiting expression of VEGF, Flt-1 or Flk-1/KDR in a subject, comprising administering an effective amount of an siRNA of the invention to the subject, such that the target mRNA is degraded. As the products of the VEGF, Flt-1 and Flk-1/KDR genes are required for initiating and maintaining angiogenesis, the invention also provides a method of inhibiting angiogenesis in a subject by the RNAi-mediated degradation of the target mRNA by the present siRNA.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the progression of angiogenesis in a subject.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA of the invention. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed by ophthalmoscopy.

Inhibition of angiogenesis can also be inferred through observing a change or reversal in a pathogenic condition associated with the angiogenesis. For example, in ARMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA of the invention.

It is understood that the siRNA of the invention can degrade the target mRNA (and thus inhibit angiogenesis) in substoichiometric amounts. Without wishing to be bound by any theory, it is believed that the siRNA of the invention causes degradation of the target mRNA in a catalytic manner. Thus, compared to standard anti-angiogenic therapies, significantly less siRNA needs to be delivered at or near the site of neovascularization to have a therapeutic effect.

One skilled in the art can readily determine an effective amount of the siRNA of the invention to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA of the invention comprises an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness.

Preferably, an siRNA of the invention is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA of the invention is used to inhibit choroidal neovascularization in age-related macular degeneration.

For treating angiogenic diseases, the siRNA of the invention can be administered to a subject in combination with a pharmaceutical agent which is different from the present siRNA. Alternatively, the siRNA of the invention can be administered to a subject in combination with another therapeutic method designed to treat the angiogenic disease. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mims Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

Preferably, the liposomes encapsulating the present siRNA comprises a ligand molecule that can target the liposome to a particular cell or tissue at or near the site of angiogenesis. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), P.N.A.S., USA, 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture such as tetrahydrofuran and water in a 30:12 ratio at 60° C.

Recombinant plasmids which express siRNA of the invention are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to an area of neovascularization in a patient are within the skill in the art.

The siRNA of the invention can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation In a preferred embodiment, injections or infusions of the siRNA are given at or near the site of neovascularization.

The siRNA of the invention can be administered in a single dose or in multiple doses. Where the administration of the siRNA of the invention is by infusion, the infusion can be a single sustained dose or can be delivered by multiple infusions. Injection of the agent directly into the tissue is at or near the site of neovascularization preferred. Multiple injections of the agent into the tissue at or near the site of neovascularization are particularly preferred.

One skilled in the art can also readily determine an appropriate dosage regimen for administering the siRNA of the invention to a given subject. For example, the siRNA can be administered to the subject once, such as by a single injection or deposition at or near the neovascularization site. Alternatively, the siRNA can be administered to a subject once or twice daily to a subject once weekly for a period of from about three to about twenty-eight days, more preferably from about seven to about ten weeks. In a preferred dosage regimen, the siRNA is injected at or near the site of neovascularization once a day for seven days.

Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science,* 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

The invention will now be illustrated with the following non-limiting examples. The animal experiments described in Examples 4-6 were performed using the University of Pennsylvania institutional guidelines for the care and use of animals in research.

EXAMPLE 1 siRNA Transfection and Hypoxia Induction In Vitro siRNA Design—A 19 nt sequence located 329 nt from the 5' end of human VEGF mRNA was chosen as a target sequence: AAACCTCACCAAGGCCAGCAC (SEQ ID NO: 51). To ensure that it was not contained in the mRNA from any other genes, this target sequence was entered into the BLAST search engine provided by NCBI. The use of the BLAST algorithm is described in Altschul et al. (1990), *J. Mol. Biol.* 215: 403-410 and Altschul et al. (1997), *Nucleic Acids Res.* 25: 3389-3402, the disclosures of which are herein incorporated by reference in their entirety. As no other mRNA was found which contained the target sequence, an siRNA duplex was synthesized to target this sequence (Dharmacon Research, Inc., Lafayette, Colo.).

The siRNA duplex had the following sense and antisense strands.

```
sense:
                            (SEQ ID NO: 77)
5'-accucaccaaggccagcacTT-3'.

antisense:
                            (SEQ ID NO: 78)
5'-gugcuggccuuggugagguTT-3'.
```

Together, the siRNA sense and antisense strands formed a 19 nt double-stranded siRNA with TT 3' overhangs (shown in bold) on each strand. This siRNA was termed "Candidate 5" or "Cand5." Other siRNA which target human VEGF mRNA were designed and tested as described for Cand5.

An siRNA targeting the following sequence in green fluorescent protein (GFP) mRNA was used as a nonspecific control: GGCTACGTCCAGCGCACC (SEQ ID NO: 79). The siRNA was purchased from Dharmacon (Lafayette, Colo.).

siRNA Transfection and Hypoxia Induction In Vitro—Human cell lines (293; Hela and ARPE19) were separately seeded into 24-well plates in 250 microliters of complete DMEM medium one day prior to transfection, so that the cells were ~50% confluent at the time of transfection. Cells were transfected with 2.5 nM Cand5 siRNA, and with either no siRNA or 2.5 nM non-specific siRNA (targeting GFP) as controls. Transfections were performed in all cell lines with the "Transit TKO Transfection" reagent, as recommended by the manufacturer (Mirus).

Twenty four hours after transfection, hypoxia was induced in the cells by the addition of desferoxamide mesylate to a final concentration of 130 micromolar in each well. Twenty four hours post-transfection, the cell culture medium was removed from all wells, and a human VEGF ELISA (R&D systems, Minneapolis, Minn.) was performed on the culture medium as described in the Quantikine human VEGF ELISA protocol available from the manufacturer, the entire disclosure of which is herein incorporated by reference.

Figure 1B:
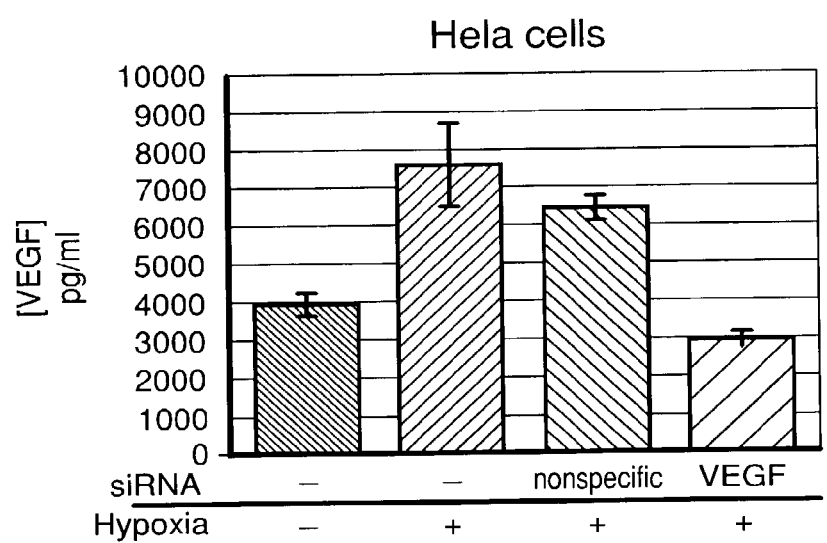

As can be seen in FIG. 1, RNAi degradation induced by Cand5 siRNA significantly reduces the concentration of VEGF produced by the hypoxic 293 and HeLa cells. There was essentially no difference in the amount of VEGF produced by hypoxic cells treated with either no siRNA or the non-specific siRNA control. Similar results were also seen with human ARPE19 cells treated under the same conditions. Thus, RNA interference with VEGF-targeted siRNA disrupts the pathogenic up-regulation of VEGF in human cultured cells in vitro.

The experiment outlined above was repeated on mouse NIH 3T3 cells using a mouse-specific VEGF siRNA (see Example 6 below), and VEGF production was quantified with a mouse VEGF ELISA (R&D systems, Minneapolis, Minn.) as described in the Quantikine mouse VEGF ELISA protocol available from the manufacturer, the entire disclosure of which is herein incorporated by reference. Results similar to those reported in FIG. 1 for the human cell lines were obtained.

EXAMPLE 2

Effect of Increasing siRNA Concentration on VEGF Production in Human Cultured Cells The experiment outlined in Example 1 was repeated with human 293, HeLa and ARPE19 cells using a range of siRNA concentrations from 10 nM to 50 nM. The ability of the Cand5 siRNA to down-regulate VEGF production increased moderately up to approximately 13 nM siRNA, but a plateau effect was seen above this concentration. These results highlight the catalytic nature of siRNA-mediated RNAi degradation of mRNA, as the plateau effect appears to reflect VEGF production from the few cells not transfected with the siRNA. For the majority of cells which had been transfected with the siRNA, the increased VEGF mRNA production induced by the hypoxia is outstripped by the siRNA-induced degradation of the target mRNA at siRNA concentrations greater than about 13 nM.

EXAMPLE 3

Specificity of siRNA Targeting

NIH 3T3 mouse fibroblasts were grown in 24-well plates under standard conditions, so that the cells were ~50% confluent one day prior to transfection. The human VEGF siRNA Cand5 was transfected into a NIH 3T3 mouse fibroblasts as in Example 1. Hypoxia was then induced in the transfected cells, and murine VEGF concentrations were measured by ELISA as in Example 1.

Figure 2:
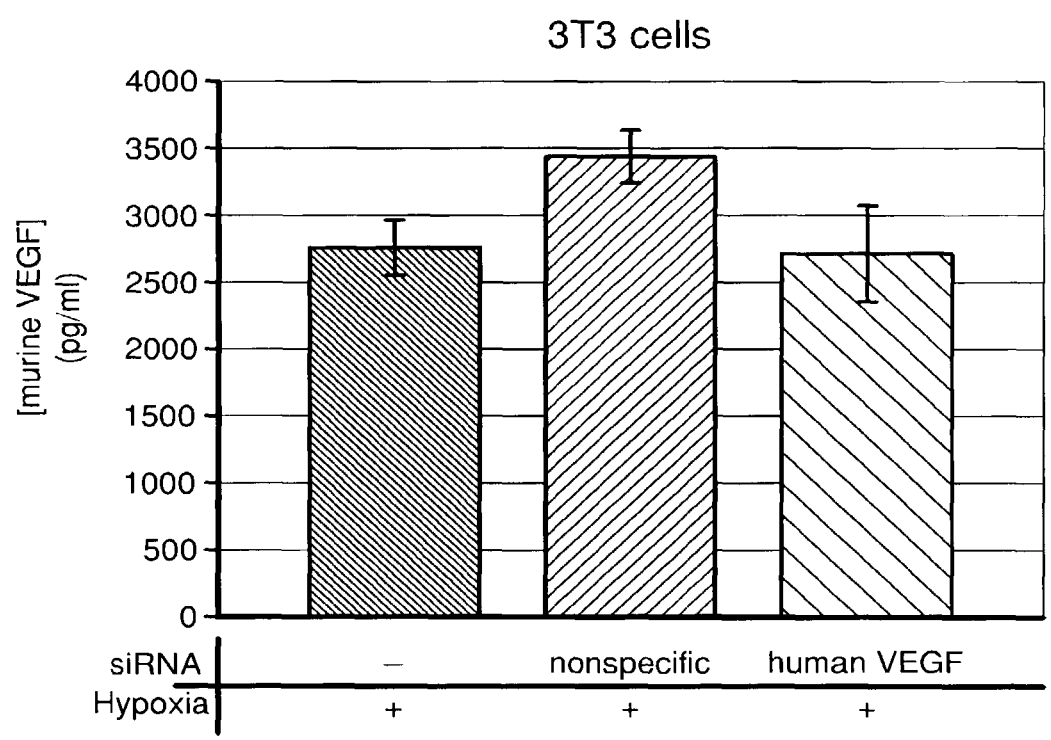
FIG. 2 is a histogram of murine VEGF concentration (in pg/ml) in hypoxic NIH 3T3 cells treated with no siRNA ("−"); nonspecific siRNA ("nonspecific"); or siRNA targeting human VEGF mRNA ("VEGF"). Each bar represents the average of six experiments and the error is the standard deviation of the mean.
Figure 3:
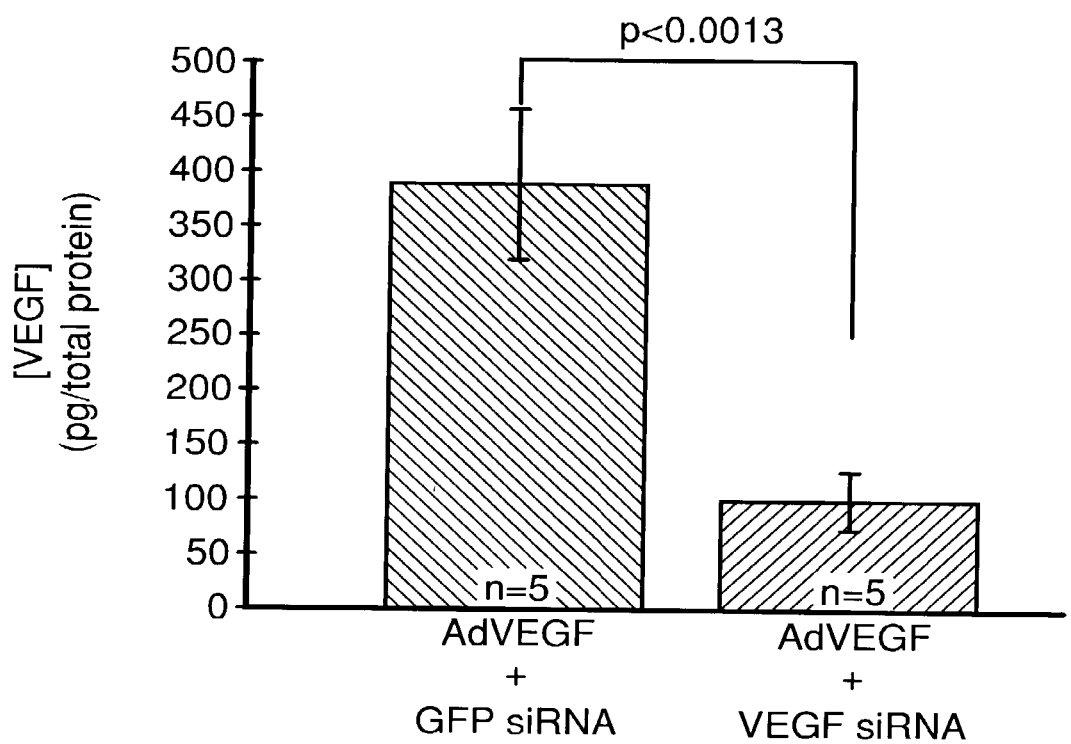
FIG. 3 is a histogram of human VEGF concentration (pg/total protein) in retinas from mice injected with adenovirus expressing human VEGF ("AdVEGF") in the presence of either GFP siRNA (dark gray bar) or human VEGF siRNA (light grey bar). Each bar represent the average of 5 eyes and the error bars represent the standard error of the mean.

The sequence targeted by the human VEGF siRNA Cand5 differs from the murine VEGF mRNA by one nucleotide. As can be seen in FIG. 2, the human VEGF siRNA has no affect on the ability of the mouse cells to up-regulate mouse VEGF after hypoxia. These results show that siRNA induced RNAi degradation is sequence-specific to within a one nucleotide resolution.

EXAMPLE 4

In Vivo Delivery of siRNA to Murine Retinal Pigment Epithelial Cells

VEGF is upregulated in the retinal pigment epithelial (RPE) cells of human patients with age-related macular degeneration (ARMD). To show that functional siRNA can be delivered to RPE cells in vivo, GFP was expressed in mouse retinas with a recombinant adenovirus, and GFP expression was silenced with siRNA. The experiment was conducted as follows.

One eye from each of five adult C57/Black6 mice (Jackson Labs, Bar Harbor, Me.) was injected subretinally as described in Bennett et al. (1996), supra., with a mixture containing ~1×10$^8$ particles of adenovirus containing eGFP driven by the CMV promoter and 20 picomoles of siRNA targeting eGFP conjugated with transit TKO reagent (Mirus).

As positive control, the contralateral eyes were injected with a mixture containing ~1×10$^8$ particles of adenovirus containing eGFP driven by the CMV promoter and 20 picomoles of siRNA targeting human VEGF conjugated with transit TKO reagent (Mirus). Expression of GFP was detected by fundus ophthalmoscopy 48 hours and 60 hours after injection. Animals were sacrificed at either 48 hours or 60 hours post-injection. The eyes were enucleated and fixed in 4% paraformaldehyde, and were prepared either as flat mounts or were processed into 10 micron cryosections for fluorescent microscopy.

No GFP fluorescence was detectable by ophthalmoscopy in the eyes which received the siRNA targeted to GFP mRNA in 4 out of 5 mice, whereas GFP fluorescence was detectable in the contralateral eye which received the non-specific control siRNA. A representative flat mount analyzed by fluorescence microscopy showed a lack of GFP fluorescence in the eye which received GFP siRNA, as compared to an eye that received the non-specific control siRNA. Cryosections of another retina showed that the recombinant adenovirus efficiently targets the RPE cells, and when the adenovirus is accompanied by siRNA targeted to GFP mRNA, expression of the GFP transgene is halted.

While there is some GFP fluorescence detectable by fluorescence microscopy in eyes that received siRNA targeted to GFP mRNA, the fluorescence is greatly suppressed as compared to controls that received non-specific siRNA. These data demonstrate that functional siRNA can be delivered in vivo to RPE cells.

EXAMPLE 5

In Vivo Expression and siRNA-Induced RNAi Degradation of Human VEGF in Murine Retinas In order to demonstrate that siRNA targeted to VEGF functioned in vivo, an exogenous human VEGF expression cassette was delivered to mouse RPE cells via an adenovirus by subretinal injection, as in Example 4. One eye received Cand5 siRNA, and the contralateral eye received siRNA targeted to GFP mRNA. The animals were sacrificed 60 hours post-injection, and the injected eyes were removed and snap frozen in liquid $N_2$ following enucleation. The eyes were then homogenized in lysis buffer, and total protein was measured using a standard Bradford protein assay (Roche, Germany). The samples were normalized for total protein prior to assaying for human VEGF by ELISA as described in Example 1.

Figure 4:
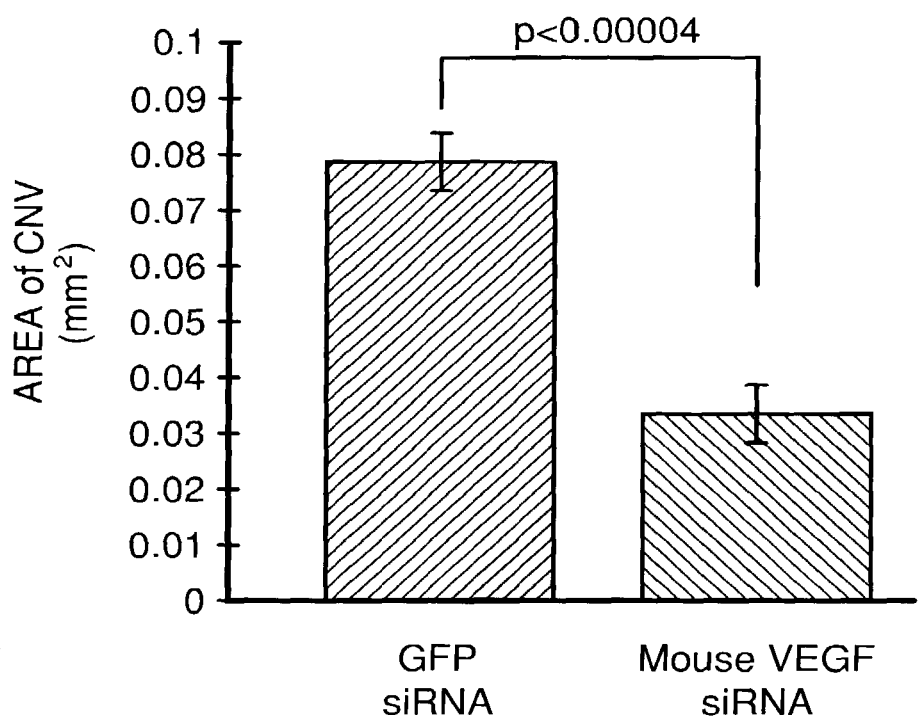
FIG. 4 is a histogram showing the mean area (in $mm^2$) of laser-induced CNV in control eyes given subretinal injections of GFP siRNA (N=9; "GFP siRNA"), and in eyes given subretinal injections of mouse VEGF siRNA (N=7; "Mouse VEGF siRNA"). The error bars represent the standard error of the mean.

The expression of VEGF was somewhat variable from animal to animal. The variability of VEGF levels correlated well to those observed in the GFP experiments of Example 4, and can be attributed to some error from injection to injection, and the differential ability of adenovirus to delivery the target gene in each animal. However, there was a significant attenuation of VEGF expression in each eye that received VEGF siRNA, as compared to the eyes receiving the non-specific control siRNA (FIG. 4). These data indicate that the Cand5 siRNA was potent and effective in silencing human VEGF expression in murine RPE cells in vivo.

EXAMPLE 6

Inhibition of Choroidal Neovascularization in the Mouse CNV Model

There is evidence that choroidal neovascularization in ARMD is due to the upregulation of VEGF in the RPE cells. This human pathologic condition can be modeled in the mouse by using a laser to burn a spot on the retina ("laser photo-coagulation" or "laser induction"). During the healing process, VEGF is believed to be up-regulated in the RPE cells of the burned region, leading to re-vascularization of the choroid. This model is called the mouse choroidal neovascularization ("CNV") model.

For rescue of the mouse CNV model, a mouse siRNA was designed that incorporated a one nucleotide change from the human "Cand5" siRNA from Example 1. The mouse siRNA specifically targeted mouse VEGF mRNA at the sequence AAACCUCACCAAAGCCAGCAC (SEQ ID NO: 80). Other siRNA that target mouse VEGF were also designed and tested. The GFP siRNA used as a nonspecific control in Example 1 was also used as a non-specific control here.

Twenty four hours after laser induction, one eye from each of eleven adult C57/Black6 mice (Jackson Labs, Bar Harbor, Me.) was injected subretinally with a mixture containing ~1×10$^8$ particles of adenovirus containing LacZ driven by the CMV promoter and 20 picomoles of siRNA targeting mouse VEGF conjugated with transit TKO reagent (Mirus), as in Example 4. As a control, contralateral eyes received a mixture containing ~1×10$^8$ particles of adenovirus containing LacZ driven by the CMV promoter and 20 picomoles of siRNA targeting GFP conjugated with transit TKO reagent (Mirus).

Fourteen days after the laser treatment, the mice were perfused with fluorescein and the area of neovascularization was measured around the burn spots. Areas of the burn spots in the contra-lateral eye were used as a control. The site of neovascularization around the burn spots in animals that received siRNA targeting mouse VEGF was, on average, ¼ the area of the control areas. These data support the use of VEGF-directed siRNA (also called "anti-VEGF siRNA") for therapy of ARMD.

EXAMPLE 7

Generation of an Adeno-Associated Viral Vector for Expression of siRNA

A "cis-acting" plasmid for generating a recombinant AAV vector for delivering an siRNA of the invention was generated by PCR based subcloning, essentially as described in Samulski R et al. (1987), supra. The cis-acting plasmid was called "pAAVsiRNA."

Figure 5:
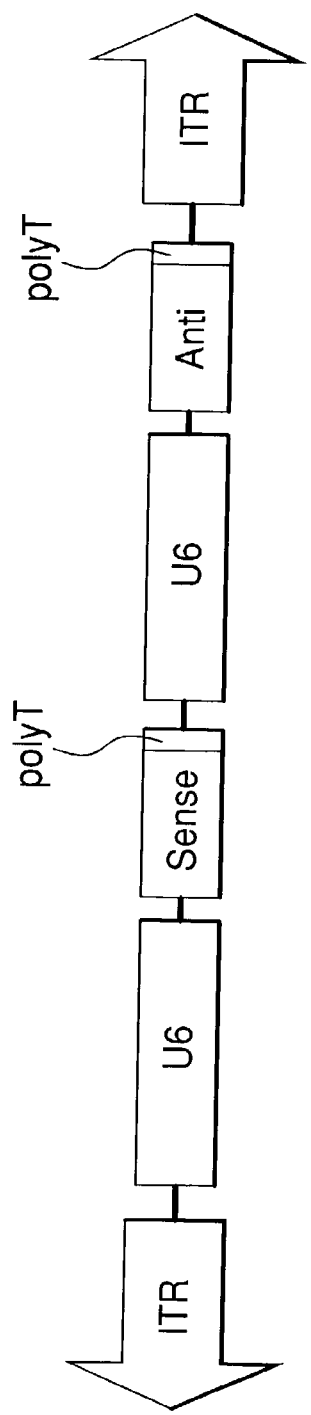
FIG. 5 is a schematic representation of pAAVsiRNA, a cis-acting plasmid used to generate a recombinant AAV viral vector of the invention. "ITR": AAV inverted terminal repeats; "U6": U6 RNA promoters; "Sense": siRNA sense coding sequence; "Anti": siRNA antisense coding sequence; "PolyT": polythymidine termination signals.

The rep and cap genes of psub201 were replaced with the following sequences in this order: a 19 nt sense RNA strand coding sequence in operable connection with a polyT termination sequence under the control of a human U6 RNA promoter, and a 19 nt antisense RNA strand coding sequence in operable connection with a polyT termination sequence under the control of a human U6 RNA promoter. A schematic representation of pAAVsiRNA is given if FIG. 5.

A recombinant AAV siRNA vector was obtained by transfecting pAAVsiRNA into human 293 cells previously infected with El-deleted adenovirus, as described in Fisher K J et al. (1996), supra. The AAV rep and cap functions were provided by a trans-acting plasmid pAAV/Ad as described in Samulski R et al. (1989), supra. Production lots of the recombinant AAV siRNA vector were titered according to the number of genome copies/ml, as described in Fisher K J et al. (1996), supra.

We claim:

1. An isolated dsRNA consisting of a 19 to 25 nucleotide sense RNA strand and a 19 to 25 nucleotide antisense RNA strand, wherein the sense and the antisense RNA strands form an RNA duplex, and wherein the antisense RNA strand consists of a nucleotide sequence that hybridizes to SEQ ID NOs: 20 or 52.

2. The dsRNA of claim 1, wherein the antisense RNA strand consists of a nucleotide sequence that hybridizes to SEQ ID NOs: 20 and 52.

3. The dsRNA of claim 1, wherein the sense and antisense RNA strands forming the RNA duplex are covalently linked by a single-stranded hairpin.

4. The dsRNA of claim 1, wherein the dsRNA further comprises non-nucleotide material.

5. The dsRNA of claim 1, wherein the sense and antisense RNA strands are stabilized against nuclease degradation.

6. The dsRNA of claim 1, wherein the RNA duplex has a 3' overhang.

7. A pharmaceutical composition comprising the dsRNA of claim 1 and a pharmaceutically acceptable carrier.

8. The pharmaceutical composition of claim 7, wherein the pharmaceutical composition further comprises a delivery reagent.

9. The pharmaceutical composition of claim 8, wherein the delivery reagent encapsulates the dsRNA.

10. The pharmaceutical composition of claim 8, wherein the delivery reagent is selected from the group consisting of lipofectin, lipofectamine, cellfectin, polycations, and liposomes.

* * * * *

SEQUENCE LISTING

<160> NUMBER OF SEQ ID NOS: 80

<210> SEQ ID NO 1
<211> LENGTH: 2250

```
<212> TYPE: DNA
<213> ORGANISM: Mus musculus

<400> SEQUENCE: 1
tgagccaggc tggcaggaag gagcctccct cagggtttcg ggaaccagac ctctcaccgg      60
aaagaccgat taaccatgtc accaccacgc catcatcgtc accgttgaca gaacagtcct     120
taatccagaa agcctgacat gaaggaagag gagactcttc gaggagcact ttgggtccgg     180
agggcgagac tccggcagac gcattccggg cagGtgacc aagcacggtc cctcgtggga     240
ctggattcgc cattttctta tatctgctgc taaatcgcca agcccggaag attagggttg     300
tttctgggat tcctgtagac acacccaccc acatacacac atatatatat attatatata     360
taaataaata tatgttttt atatataaaa tatatatata ttcttttttt taaattaact     420
ctgctaatgt tattggtgtc ttcactggat atgtttgact gctgtggact tgtgttggga     480
ggaggatgtc ctcactcgga tgccgacatg ggagacaatg ggatgaaagg cttcagtgtg     540
gtctgagaga ggccgaagtc cttttgcctg ccggggagca agcaaggcca gggcacgggg     600
gcacattggc tcacttccag aaacacgaca aacccattcc tggccctgag tcaagaggac     660
agagagacag atgatgacac agaaagagat aaagatgccg gttccaacca gaagtttggg     720
gagcctcagg acatggcatg ctttgtggat ccccatgata gtctacaaaa gcaccccgcc     780
cctctgggca ctgcctggaa gaatcgggag cctggccagc cttcagctcg ctcctccact     840 tctgagggc ctaggaggcc tcccacaggt gtccggcaa gagaagacac ggtggtggaa     900
gaagaggcct ggtaatggcc cctcctcctg ggaccccttc gtcctctcct taccccacct     960
cctgggtaca gcccaggagg accttgtgtg atcagaccat tgaaaccact aattctgtcc    1020
ccaggagact tggctctgtg tgtgagtggc ttacccttcc tcatcttccc ttcccaaggc    1080
acagagcaat ggggcaggac ccgcaagccc ctcacggagg cagagaaaag agaaagtgtt    1140
ttatatacgg tacttattta atagcccttt ttaattagaa attaaaacag ttaatttaat    1200
taaagagtag ggttttttc agtattcttg gttaatattt aatttcaact atttatgaga    1260
tgtatctctc gctctctctt atttgtactt atgtgtgtgt gtgtgtgtgt gtgtgtgtgt    1320
gtgtgtgtgt gtatgaaatc tgtgtttcca atctctctct cccagatcgg tgacagtcac    1380
tagcttgtcc tgagaagata tttaattttg ctaacactca gctctgccct cccttgtccc    1440
caccacacat tcctttgaaa taaggtttca atatacattt acatactata tatatatttg    1500
gcaacttgtg tttgtatata aatatatata tatatatatg tttatgtata tatgtgattc    1560
tgataaaata gacattgcta ttctgttttt tatatgtaaa aacaaaacaa gaaaaataga    1620
gaattctaca tactaaatct ctctcctttt ttaattttaa tatttgttat catttattta    1680
ttggtgctac tgtttatccg taataattgt gggggaaaaa gatattaaca tcacgtcttt    1740
gtctctagag cagttttccg agatattccg tagtacatat ttattttaa acagcaacaa    1800 agaaatacag atatatctta aaaaaaagc attttgtatt aaagaattga attctgatct    1860
caaagctctc cctggtctct ccttctctcc tgggccctcc tgtctcgctt tcctcctcc    1920 tttgggtac atagttttg tcttaggttt gagaagcagt ccctggagta gaatatgggg    1980
tgacccatcc attcctgggc ggaggggaga tggctccttt gccaagggtc ctcacactac    2040
gtggtactct gttccttgtc agacaaggat gggggcatgt ctccaggtgc taactggaga    2100
tcggagagag ctgttggctg cagctggcca ggatttgggc atgccgggga catgggaggc    2160
tgtgagccca gcatgcagtt tacttctggg tgctaaatgg aagagtccag taaaaagagt    2220
```

```
cttgcccatg ggattccatt ccgctttgtg                                      2250
```

<210> SEQ ID NO 2
<211> LENGTH: 444
<212> TYPE: DNA
<213> ORGANISM: Homo sapiens

<400> SEQUENCE: 2

```
atgaactttc tgctgtcttg ggtgcattgg agccttgcct tgctgctcta cctccaccat     60
gccaagtggt cccaggctgc acccatggca gaaggaggag gcagaatca tcacgaagtg     120
gtgaagttca tggatgtcta tcagcgcagc tactgccatc caatcgagac cctggtggac    180
atcttccagg agtaccctga tgagatcgag tacatcttca gccatcctg tgtgcccctg     240
atgcgatgcg ggggctgctg caatgacgag ggcctggagt gtgtgcccac tgaggagtcc    300
aacatcacca tgcagattat gcggatcaaa cctcaccaag ccagcacat aggagagatg     360
agcttcctac agcacaacaa atgtgaatgc agaccaaaga agatagagc aagacaagaa     420
aaatgtgaca agccgaggcg gtga                                           444
```

<210> SEQ ID NO 3
<211> LENGTH: 576
<212> TYPE: DNA
<213> ORGANISM: Homo sapiens

<400> SEQUENCE: 3

```
atgaactttc tgctgtcttg ggtgcattgg agccttgcct tgctgctcta cctccaccat     60
gccaagtggt cccaggctgc acccatggca gaaggaggag gcagaatca tcacgaagtg     120
gtgaagttca tggatgtcta tcagcgcagc tactgccatc caatcgagac cctggtggac    180
atcttccagg agtaccctga tgagatcgag tacatcttca gccatcctg tgtgcccctg     240
atgcgatgcg ggggctgctg caatgacgag ggcctggagt gtgtgcccac tgaggagtcc    300
aacatcacca tgcagattat gcggatcaaa cctcaccaag ccagcacat aggagagatg     360
agcttcctac agcacaacaa atgtgaatgc agaccaaaga agatagagc aagacaagaa     420
aatcccgtgt ggccttgctc agagcggaga aagcatttgt ttgtacaaga tccgcagacg    480
tgtaaatgtt cctgcaaaaa cacagactcg cgttgcaagg cgaggcagct tgagttaaac    540
gaacgtactt gcagatgtga caagccgagg cggtga                              576
```

<210> SEQ ID NO 4
<211> LENGTH: 648
<212> TYPE: DNA
<213> ORGANISM: Homo sapiens

<400> SEQUENCE: 4

```
atgaactttc tgctgtcttg ggtgcattgg agccttgcct tgctgctcta cctccaccat     60
gccaagtggt cccaggctgc acccatggca gaaggaggag gcagaatca tcacgaagtg     120
gtgaagttca tggatgtcta tcagcgcagc tactgccatc caatcgagac cctggtggac    180
atcttccagg agtaccctga tgagatcgag tacatcttca gccatcctg tgtgcccctg     240
atgcgatgcg ggggctgctg caatgacgag ggcctggagt gtgtgcccac tgaggagtcc    300
aacatcacca tgcagattat gcggatcaaa cctcaccaag ccagcacat aggagagatg     360
agcttcctac agcacaacaa atgtgaatgc agaccaaaga agatagagc aagacaagaa     420
aaaaaatcag ttcgaggaaa gggaaggggg caaaaacgaa agcgcaagaa atcccggtat    480
aagtcctgga gcgttccctg tgggccttgc tcagagcgga gaaagcattt gtttgtacaa    540
```

| | |
|---|---|
| gatccgcaga cgtgtaaatg ttcctgcaaa aacacagact cgcgttgcaa ggcgaggcag | 600 |
| cttgagttaa acgaacgtac ttgcagatgt gacaagccga ggcggtga | 648 |

<210> SEQ ID NO 5
<211> LENGTH: 670
<212> TYPE: DNA
<213> ORGANISM: Homo sapiens

<400> SEQUENCE: 5

| | |
|---|---|
| gccttgctgc tctacctcca ccatgccaag tggtcccagg ctgcaccat ggcagaagga | 60 |
| ggagggcaga atcatcacga agtggtgaag ttcatggatg tctatcagcg cagctactgc | 120 |
| catccaatcg agaccctggt ggacatcttc caggagtacc ctgatgagat cgagtacatc | 180 |
| ttcaagccat cctgtgtgcc cctgatgcga tgcgggggct gctgcaatga cgagggcctg | 240 |
| gagtgtgtgc ccactgagga gtccaacatc accatgcaga ttatgcggat caaacctcac | 300 |
| caaggccagc ataggagaa gatgagcttc ctacagcaca caaatgtga atgcagacca | 360 |
| aagaaggata gagcaagaca agaaaaaaaa tcagttcgag aaagggaaa ggggcaaaaa | 420 |
| cgaaagcgca agaaatcccg gtataagtcc tggagcgttt acgttggtgc ccgctgctgt | 480 |
| ctaatgccct ggagcctccc tggcccccat ccctgtgggc cttgctcaga gcggagaaag | 540 |
| catttgtttg tacaagatcc gcagacgtgt aaatgttcct gcaaaacac agactcgcgt | 600 |
| tgcaaggcga ggcagcttga gttaaacgaa cgtacttgca gatgtgacaa gccgaggcgg | 660 |
| tgatgaatga | 670 |

<210> SEQ ID NO 6
<211> LENGTH: 1137
<212> TYPE: DNA
<213> ORGANISM: Homo sapiens

<400> SEQUENCE: 6

| | |
|---|---|
| atgctcattg tccagactgg ggtcagatca gcaaacaaag ggcctctgat ggtgattgtt | 60 |
| gaatattgca aatatggaaa tctatccaac tacctcaaga gcaaatatga cttattttt | 120 |
| ctcgacaagg atgtggcatc acacatggag cgtaagaaag aaaaaatgga gccaggcctg | 180 |
| gaacaaggca agaaaccaaa actagatagc atcaccagca gcgagagctt gggagctcc | 240 |
| aagtttcagg aagataaaaa tctgagtgat gttgaggaag aggaggattc tgatggtttc | 300 |
| taccaggagc ccatcactat ggaagatctg attcttaca gttttcaagt ggccagaggc | 360 |
| atgaagtttc tgtcttccag aaagtgcatt cattgggacc tggcagcaag aaacattctt | 420 |
| ttatctgaga caatgtggt gaagatttgt gattttggcc ttgcccagga tatttacaag | 480 |
| aacgccgatt atgtgagaaa aggaggtggg tctccatacc aggagtgca atggatgag | 540 |
| cacttctgca gttgcctgag ggaaggcatg aggatgagag ctgctgagta ctccactcct | 600 |
| gaaatctatc agatcatgct ggactgcagg cacaaagacc caaagaaag gccaagattt | 660 |
| gcagaacttg tggaaaaact agaaaatagt gggtttacat actcaactcc tgccttctct | 720 |
| gaggacttct tcaaggaagg tatttcagct cccaagttta gttcaggaag ctctgatgat | 780 |
| gtcagatacg taaatgcttt caagttcatg agcctgaaa gaatcaaaac cttttgaagaa | 840 |
| cttttgccaa atgccacctc catgtttgat gactaccagg gggacagcag cgctctgctg | 900 |
| gcctctccca tgctgaagcg cttcaccagg actgacagca aacccaaggc ctcgctcaag | 960 |
| attgacttga gactaactag caaaagtaag aagtcggggc tttctgatgt cagcaggccc | 1020 |

| | |
|---|---|
| agtttctgcc attccaacag tgggcacatc agcaaaggca agggcaggtt cacctacgac | 1080 |
| aacgccgagc tggaaaggaa gacggcgtgc tgctccccgc ccctctggga gttgtag | 1137 |

<210> SEQ ID NO 7
<211> LENGTH: 5830
<212> TYPE: DNA
<213> ORGANISM: Homo sapiens

<400> SEQUENCE: 7

| | |
|---|---|
| actgagtccc gggaccccgg gagagcggtc agtgtgtggt cgctgcgttt cctctgcctg | 60 |
| cgccgggcat cacttgcgcg ccgcagaaag tccgtctggc agcctggata tcctctccta | 120 |
| ccggcacccg cagacgcccc tgcagccgcc ggtcggcgcc cgggctccct agccctgtgc | 180 |
| gctcaactgt cctgcgctgc ggggtgccgc gagttccacc tccgcgcctc cttctctaga | 240 |
| caggcgctgg gagaaagaac cggctcccga gttctgggca tttcgcccgg ctcgaggtgc | 300 |
| aggatgcaga gcaaggtgct gctggccgtc gccctgtggc tctgcgtgga gacccgggcc | 360 |
| gcctctgtgg gtttgcctag tgtttctctt gatctgccca ggctcagcat acaaaaagac | 420 |
| atacttacaa ttaaggctaa tacaactctt caaattactt gcaggggaca gagggacttg | 480 |
| gactggcttt ggcccaataa tcagagtggc agtgagcaaa gggtggaggt gactgagtgc | 540 |
| agcgatggcc tcttctgtaa gacactcaca attccaaaag tgatcggaaa tgacactgga | 600 |
| gcctacaagt gcttctaccg ggaaactgac ttggcctcgg tcatttatgt ctatgttcaa | 660 |
| gattacagat ctccattat tgcttctgtt agtgaccaac atggagtcgt gtacattact | 720 |
| gagaacaaaa acaaaactgt ggtgattcca tgtctcgggt ccatttcaaa tctcaacgtg | 780 |
| tcactttgtg caagataccc agaaaagaga tttgttcctg atggtaacag aatttcctgg | 840 |
| gacagcaaga agggctttac tattcccagc tacatgatca gctatgctgg catggtcttc | 900 |
| tgtgaagcaa aaattaatga tgaaagttac cagtctatta tgtacatagt tgtcgttgta | 960 |
| gggtatagga tttatgatgt ggttctgagt ccgtctcatg gaattgaact atctgttgga | 1020 |
| gaaaagcttg tcttaaattg tacagcaaga actgaactaa atgtggggat tgacttcaac | 1080 |
| tgggaatacc cttcttcgaa gcatcagcat aagaaacttg taaaccgaga cctaaaaacc | 1140 |
| cagtctggga gtgagatgaa gaaattttg agcaccttaa ctatagatgg tgtaacccgg | 1200 |
| agtgaccaag gattgtacac ctgtgcagca tccagtgggc tgatgaccaa gaagaacagc | 1260 |
| acatttgtca gggtccatga aaaaccttt gttgcttttg aagtggcat ggaatctctg | 1320 |
| gtggaagcca cggtgggga gcgtgtcaga atccctgcga agtaccttgg ttacccaccc | 1380 |
| ccagaaataa aatggtataa aaatggaata ccccttgagt ccaatcacac aattaaagcg | 1440 |
| gggcatgtac tgacgattat ggaagtgagt gaaagagaca caggaaatta cactgtcatc | 1500 |
| cttaccaatc ccatttcaaa ggagaagcag agccatgtgg tctctctggt tgtgtatgtc | 1560 |
| ccaccccaga ttggtgagaa atctctaatc tctcctgtgg attcctacca gtacggcacc | 1620 |
| actcaaacgc tgacatgtac ggtctatgcc attcctcccc gcatcacat ccactggtat | 1680 |
| tggcagttgg aggaagagtg cgccaacgag cccagccaag ctgtctcagt gacaaaccca | 1740 |
| taccttgtg aagaatggag aagtgtggag gacttccagg gaggaaataa aattgaagtt | 1800 |
| aataaaaatc aatttgctct aattgaagga aaaacaaaa ctgtaagtac ccttgttatc | 1860 |
| caagcggcaa atgtgtcagc tttgtacaaa tgtgaagcgg tcaacaaagt cgggagagga | 1920 |
| gagagggtga tctccttcca cgtgaccagg ggtcctgaaa ttacttttgca acctgacatg | 1980 |
| cagcccactg agcaggagag cgtgtctttg tggtgcactg cagacagatc tacgtttgag | 2040 |

```
aacctcacat ggtacaagct tggcccacag cctctgccaa tccatgtggg agagttgccc    2100
acacctgttt gcaagaactt ggatactctt tggaaattga atgccaccat gttctctaat    2160
agcacaaatg acattttgat catggagctt aagaatgcat ccttgcagga ccaaggagac    2220
tatgtctgcc ttgctcaaga caggaagacc aagaaaagac attgcgtggt caggcagctc    2280
acagtcctag agcgtgtggc acccacgatc acaggaaacc tggagaatca gacgacaagt    2340 attgggaaa gcatcgaagt ctcatgcacg gcatctggga atcccctcc acagatcatg     2400 tggtttaaag ataatgagac ccttgtagaa gactcaggca ttgtattgaa ggatgggaac    2460
cggaacctca ctatccgcag agtgaggaag gaggacgaag cctctacac ctgccaggca     2520 tgcagtgttc ttggctgtgc aaaagtggag gcattttttca taatagaagg tgcccaggaa   2580
aagacgaact tggaaatcat tattctagta ggcacggcgg tgattgccat gttcttctgg    2640
ctacttcttg tcatcatcct acggaccgtt aagcgggcca atggagggga actgaagaca    2700
ggctacttgt ccatcgtcat ggatccagat gaactcccat tggatgaaca ttgtgaacga    2760
ctgccttatg atgccagcaa atgggaattc cccagagacc ggctgaagct aggtaagcct    2820
cttggccgtg gtgcctttgg ccaagtgatt gaagcagatg cctttggaat tgacaagaca    2880
gcaacttgca ggacagtagc agtcaaaatg ttgaaagaag gagcaacaca cagtgagcat    2940
cgagctctca tgtctgaact caagatcctc attcatattg gtcaccatct caatgtggtc    3000
aaccttctag gtgcctgtac caagccagga gggccactca tggtgattgt ggaattctgc    3060
aaatttggaa acctgtccac ttacctgagg agcaagagaa atgaatttgt ccctacaag    3120 accaaagggg cacgattccg tcaagggaaa gactacgttg gagcaatccc tgtggatctg    3180
aaacggcgct tggacagcat caccagtagc cagagctcag ccagtctgg atttgtggag     3240 gagaagtccc tcagtgatgt agaagaagag gaagctcctg aagatctgta taaggacttc    3300
ctgaccttgg agcatctcat ctgttacagc ttccaagtgg ctaagggcat ggagttcttg    3360
gcatcgcgaa agtgtatcca cagggacctg gcggcacgaa atatcctctt atcggagaag    3420
aacgtggtta aaatctgtga ctttggcttg gcccgggata tttataaaga tccagattat    3480
gtcagaaaag gagatgctcg cctccctttg aaatggatgg cccagaaaac aattttttgac   3540 agagtgtaca caatccagag tgacgtctgg tcttttggtg ttttgctgtg ggaaatattt    3600
tccttaggtg cttctccata tcctgggta agattgatg aagaatttgt taggcgattg      3660
aaagaaggaa ctagaatgag ggcccctgat tatactacac agaaatgta ccagaccatg     3720 ctggactgct ggcacgggga gcccagtcag agacccacgt tttcagagtt ggtggaacat    3780
ttgggaaatc tcttgcaagc taatgctcag caggatggca agactacat tgttcttccg      3840 atatcagaga ctttgagcat ggaagaggat tctggactct ctctgcctac ctcacctgtt    3900
tcctgtatgg aggaggagga agtatgtgac cccaaattcc attatgacaa cacagcagga    3960
atcagtcagt atctgcagaa cagtaagcga aagagccggc ctgtgagtgt aaaaacattt    4020
gaagatatcc cgttagaaga accagaagta aaagtaatcc cagatgacaa ccagacggac    4080
agtggtatgg ttcttgcctc agaagagctg aaaactttgg aagacagaac caaattatct    4140 ccatctttttg gtgaatggt gcccagcaaa agcagggagt ctgtggcatc tgaaggctca    4200
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt ttaaaaggaa    4380
```

```
gcatccacac cccaactccc ggacatcaca tgagaggtct gctcagattt tgaagtgttg      4440
ttctttccac cagcaggaag tagccgcatt tgattttcat ttcgacaaca gaaaaaggac      4500
ctcggactgc agggagccag tcttctaggc atatcctgga agaggcttgt gacccaagaa      4560
tgtgtctgtg tcttctccca gtgttgacct gatcctcttt tttcattcat ttaaaaagca      4620
ttatcatgcc cctgctgcgg gtctcaccat gggtttagaa caaagagctt caagcaatgg      4680
ccccatcctc aaagaagtag cagtacctgg ggagctgaca cttctgtaaa actagaagat      4740
aaaccaggca acgtaagtgt tcgaggtgtt gaagatggga aggatttgca gggctgagtc      4800
tatccaagag gctttgttta ggacgtgggt cccaagccaa gccttaagtg tggaattcgg      4860
attgatagaa aggaagacta acgttacctt gctttggaga gtactggagc ctgcaaatgc      4920
attgtgtttg ctctggtgga ggtgggcatg gggtctgttc tgaaatgtaa agggttcaga      4980
cggggtttct ggttttagaa ggttgcgtgt tcttcgagtt gggctaaagt agagttcgtt      5040
gtgctgtttc tgactcctaa tgagagttcc ttccagaccg ttagctgtct ccttgccaag      5100
ccccaggaag aaaatgatgc agctctggct ccttgtctcc caggctgatc ctttattcag      5160
aataccacaa agaaaggaca ttcagctcaa ggctccctgc cgtgttgaag agttctgact      5220
gcacaaacca gcttctggtt tcttctggaa tgaataccct catatctgtc ctgatgtgat      5280
atgtctgaga ctgaatgcgg gaggttcaat gtgaagctgt gtgtggtgtc aaagtttcag      5340
gaaggatttt acccttttgt tcttccccct gtccccaacc cactctcacc ccgcaaccca      5400
tcagtatttt agttatttgg cctctactcc agtaaacctg attgggtttg ttcactctct      5460
gaatgattat tagccagact tcaaaattat tttatagccc aaattataac atctattgta      5520
ttatttagac ttttaacata tagagctatt tctactgatt tttgcccttg ttctgtcctt      5580
tttttcaaaa aagaaaatgt gttttttgtt tggtaccata gtgtgaaatg ctgggaacaa      5640
tgactataag acatgctatg gcacatatat ttatagtctg tttatgtaga acaaatgta       5700 atatattaaa gccttatata taatgaactt tgtactattc acattttgta tcagtattat      5760
gtagcataac aaaggtcata atgctttcag caattgatgt cattttatta aagaacattg      5820
aaaaacttga                                                              5830
```

<210> SEQ ID NO 8
<211> LENGTH: 19
<212> TYPE: DNA
<213> ORGANISM: Artificial Sequence
<220> FEATURE:
<223> OTHER INFORMATION: Targeting Sequence

<400> SEQUENCE: 8
tcatcacgaa gtggtgaag                                                   19

<210> SEQ ID NO 9
<211> LENGTH: 21
<212> TYPE: RNA
<213> ORGANISM: Artificial Sequence
<220> FEATURE:
<223> OTHER INFORMATION: Sense strand

<400> SEQUENCE: 9
ucaucacgaa guggugaagu u                                                21

<210> SEQ ID NO 10
<211> LENGTH: 21
<212> TYPE: RNA
<213> ORGANISM: Artificial Sequence

```
<220> FEATURE:
<223> OTHER INFORMATION: Antisense strand

<400> SEQUENCE: 10
cuucaccacu ucgugaugau u                                             21

<210> SEQ ID NO 11
<211> LENGTH: 21
<212> TYPE: DNA
<213> ORGANISM: Artificial Sequence
<220> FEATURE:
<223> OTHER INFORMATION: Sense strand
<220> FEATURE:
<221> NAME/KEY: misc_RNA
<222> LOCATION: (1)...(19)
<223> OTHER INFORMATION: ribonucleotide
<220> FEATURE:
<221> NAME/KEY: misc_feature
<222> LOCATION: (20)...(21)
<223> OTHER INFORMATION: deoxyribonucleotide

<400> SEQUENCE: 11
ucaucacgaa guggugaagt t                                             21

<210> SEQ ID NO 12
<211> LENGTH: 21
<212> TYPE: DNA
<213> ORGANISM: Artificial Sequence
<220> FEATURE:
<223> OTHER INFORMATION: Antisense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 12
cuucaccacu ucgugaugat t                                             21

<210> SEQ ID NO 13
<211> LENGTH: 21
<212> TYPE: DNA
<213> ORGANISM: Artificial Sequence
<220> FEATURE:
<223> OTHER INFORMATION: Targeting Sequence

<400> SEQUENCE: 13
aacgtacttg cagatgtgac a                                             21

<210> SEQ ID NO 14
<211> LENGTH: 19
<212> TYPE: DNA
<213> ORGANISM: Artificial Sequence
<220> FEATURE:
<223> OTHER INFORMATION: Targeting Sequence

<400> SEQUENCE: 14
gttcatggat gtctatcag                                                19

<210> SEQ ID NO 15
<211> LENGTH: 19
<212> TYPE: DNA
<213> ORGANISM: Artificial Sequence
<220> FEATURE:
<223> OTHER INFORMATION: Targeting Sequence
```

```
<400> SEQUENCE: 15
tcgagaccct ggtggacat                                               19

<210> SEQ ID NO 16
<211> LENGTH: 19
<212> TYPE: DNA
<213> ORGANISM: Artificial Sequence
<220> FEATURE:
<223> OTHER INFORMATION: Targeting Sequence

<400> SEQUENCE: 16
tgacgagggc ctggagtgt                                               19

<210> SEQ ID NO 17
<211> LENGTH: 19
<212> TYPE: DNA
<213> ORGANISM: Artificial Sequence
<220> FEATURE:
<223> OTHER INFORMATION: Targeting Sequence

<400> SEQUENCE: 17
tgacgagggc ctggagtgt                                               19

<210> SEQ ID NO 18
<211> LENGTH: 19
<212> TYPE: DNA
<213> ORGANISM: Artificial Sequence
<220> FEATURE:
<223> OTHER INFORMATION: Targeting Sequence

<400> SEQUENCE: 18
catcaccatg cagattatg                                               19

<210> SEQ ID NO 19
<211> LENGTH: 19
<212> TYPE: DNA
<213> ORGANISM: Artificial Sequence
<220> FEATURE:
<223> OTHER INFORMATION: Targeting Sequence

<400> SEQUENCE: 19
acctcaccaa ggccagcac                                               19

<210> SEQ ID NO 20
<211> LENGTH: 19
<212> TYPE: DNA
<213> ORGANISM: Artificial Sequence
<220> FEATURE:
<223> OTHER INFORMATION: Targeting Sequence

<400> SEQUENCE: 20
ggccagcaca taggagaga                                               19

<210> SEQ ID NO 21
<211> LENGTH: 19
<212> TYPE: DNA
<213> ORGANISM: Artificial Sequence
<220> FEATURE:
<223> OTHER INFORMATION: Targeting Sequence

<400> SEQUENCE: 21
caaatgtgaa tgcagacca                                               19

<210> SEQ ID NO 22
<211> LENGTH: 19
```

```
<212> TYPE: DNA
<213> ORGANISM: Artificial Sequence
<220> FEATURE:
<223> OTHER INFORMATION: Targeting Sequence

<400> SEQUENCE: 22
atgtgaatgc agaccaaag                                              19

<210> SEQ ID NO 23
<211> LENGTH: 19
<212> TYPE: DNA
<213> ORGANISM: Artificial Sequence
<220> FEATURE:
<223> OTHER INFORMATION: Targeting Sequence

<400> SEQUENCE: 23
tgcagaccaa agaaagata                                              19

<210> SEQ ID NO 24
<211> LENGTH: 19
<212> TYPE: DNA
<213> ORGANISM: Artificial Sequence
<220> FEATURE:
<223> OTHER INFORMATION: Targeting Sequence

<400> SEQUENCE: 24
agaaagatag agcaagaca                                              19

<210> SEQ ID NO 25
<211> LENGTH: 19
<212> TYPE: DNA
<213> ORGANISM: Artificial Sequence
<220> FEATURE:
<223> OTHER INFORMATION: Targeting Sequence

<400> SEQUENCE: 25
gaaagataga gcaagacaa                                              19

<210> SEQ ID NO 26
<211> LENGTH: 19
<212> TYPE: DNA
<213> ORGANISM: Artificial Sequence
<220> FEATURE:
<223> OTHER INFORMATION: Targeting Sequence

<400> SEQUENCE: 26
gatagagcaa gacaagaaa                                              19

<210> SEQ ID NO 27
<211> LENGTH: 19
<212> TYPE: DNA
<213> ORGANISM: Artificial Sequence
<220> FEATURE:
<223> OTHER INFORMATION: Targeting Sequence

<400> SEQUENCE: 27
gacaagaaaa tccctgtgg                                              19

<210> SEQ ID NO 28
<211> LENGTH: 19
<212> TYPE: DNA
<213> ORGANISM: Artificial Sequence
<220> FEATURE:
<223> OTHER INFORMATION: Targeting Sequence

<400> SEQUENCE: 28
```
gaaaatccct gtgggcctt                                                 19

<210> SEQ ID NO 29
<211> LENGTH: 19
<212> TYPE: DNA
<213> ORGANISM: Artificial Sequence
<220> FEATURE:
<223> OTHER INFORMATION: Targeting Sequence

<400> SEQUENCE: 29
aatccctgtg ggccttgct                                                 19

<210> SEQ ID NO 30
<211> LENGTH: 19
<212> TYPE: DNA
<213> ORGANISM: Artificial Sequence
<220> FEATURE:
<223> OTHER INFORMATION: Targeting Sequence

<400> SEQUENCE: 30
tccctgtggg ccttgctca                                                 19

<210> SEQ ID NO 31
<211> LENGTH: 19
<212> TYPE: DNA
<213> ORGANISM: Artificial Sequence
<220> FEATURE:
<223> OTHER INFORMATION: Targeting Sequence

<400> SEQUENCE: 31
gcatttgttt gtacaagat                                                 19

<210> SEQ ID NO 32
<211> LENGTH: 19
<212> TYPE: DNA
<213> ORGANISM: Artificial Sequence
<220> FEATURE:
<223> OTHER INFORMATION: Targeting Sequence

<400> SEQUENCE: 32
gatccgcaga cgtgtaaat                                                 19

<210> SEQ ID NO 33
<211> LENGTH: 19
<212> TYPE: DNA
<213> ORGANISM: Artificial Sequence
<220> FEATURE:
<223> OTHER INFORMATION: Targeting Sequence

<400> SEQUENCE: 33
atgttcctgc aaaaacaca                                                 19

<210> SEQ ID NO 34
<211> LENGTH: 19
<212> TYPE: DNA
<213> ORGANISM: Artificial Sequence
<220> FEATURE:
<223> OTHER INFORMATION: Targeting Sequence

<400> SEQUENCE: 34
tgttcctgca aaaacacag                                                 19

<210> SEQ ID NO 35
<211> LENGTH: 19
<212> TYPE: DNA
<213> ORGANISM: Artificial Sequence

```
<220> FEATURE:
<223> OTHER INFORMATION: Targeting Sequence

<400> SEQUENCE: 35
aaacacagac tcgcgttgc                                                19

<210> SEQ ID NO 36
<211> LENGTH: 19
<212> TYPE: DNA
<213> ORGANISM: Artificial Sequence
<220> FEATURE:
<223> OTHER INFORMATION: Targeting Sequence

<400> SEQUENCE: 36
aacacagact cgcgttgca                                                19

<210> SEQ ID NO 37
<211> LENGTH: 19
<212> TYPE: DNA
<213> ORGANISM: Artificial Sequence
<220> FEATURE:
<223> OTHER INFORMATION: Targeting Sequence

<400> SEQUENCE: 37
acacagactc gcgttgcaa                                                19

<210> SEQ ID NO 38
<211> LENGTH: 19
<212> TYPE: DNA
<213> ORGANISM: Artificial Sequence
<220> FEATURE:
<223> OTHER INFORMATION: Targeting Sequence

<400> SEQUENCE: 38
cacagactcg cgttgcaag                                                19

<210> SEQ ID NO 39
<211> LENGTH: 19
<212> TYPE: DNA
<213> ORGANISM: Artificial Sequence
<220> FEATURE:
<223> OTHER INFORMATION: Targeting Sequence

<400> SEQUENCE: 39
ggcgaggcag cttgagtta                                                19

<210> SEQ ID NO 40
<211> LENGTH: 19
<212> TYPE: DNA
<213> ORGANISM: Artificial Sequence
<220> FEATURE:
<223> OTHER INFORMATION: Targeting Sequence

<400> SEQUENCE: 40
acgaacgtac ttgcagatg                                                19

<210> SEQ ID NO 41
<211> LENGTH: 19
<212> TYPE: DNA
<213> ORGANISM: Artificial Sequence
<220> FEATURE:
<223> OTHER INFORMATION: Targeting Sequence

<400> SEQUENCE: 41
cgaacgtact tgcagatgt                                                19
```

<210> SEQ ID NO 42
<211> LENGTH: 19
<212> TYPE: DNA
<213> ORGANISM: Artificial Sequence
<220> FEATURE:
<223> OTHER INFORMATION: Targeting Sequence

<400> SEQUENCE: 42
cgtacttgca gatgtgaca                                                19

<210> SEQ ID NO 43
<211> LENGTH: 19
<212> TYPE: DNA
<213> ORGANISM: Artificial Sequence
<220> FEATURE:
<223> OTHER INFORMATION: Targeting Sequence

<400> SEQUENCE: 43
gtggtcccag gctgcaccc                                                19

<210> SEQ ID NO 44
<211> LENGTH: 19
<212> TYPE: DNA
<213> ORGANISM: Artificial Sequence
<220> FEATURE:
<223> OTHER INFORMATION: Targeting Sequence

<400> SEQUENCE: 44
ggaggagggc agaatcatc                                                19

<210> SEQ ID NO 45
<211> LENGTH: 19
<212> TYPE: DNA
<213> ORGANISM: Artificial Sequence
<220> FEATURE:
<223> OTHER INFORMATION: Targeting Sequence

<400> SEQUENCE: 45
gtggtgaagt tcatggatg                                                19

<210> SEQ ID NO 46
<211> LENGTH: 21
<212> TYPE: DNA
<213> ORGANISM: Artificial Sequence
<220> FEATURE:
<223> OTHER INFORMATION: Targeting Sequence

<400> SEQUENCE: 46
aatcatcacg aagtggtgaa g                                             21

<210> SEQ ID NO 47
<211> LENGTH: 21
<212> TYPE: DNA
<213> ORGANISM: Artificial Sequence
<220> FEATURE:
<223> OTHER INFORMATION: Targeting Sequence

<400> SEQUENCE: 47
aagttcatgg atgtctatca g                                             21

<210> SEQ ID NO 48
<211> LENGTH: 21
<212> TYPE: DNA
<213> ORGANISM: Artificial Sequence
<220> FEATURE:
<223> OTHER INFORMATION: Targeting Sequence

```
<400> SEQUENCE: 48
aatcgagacc ctggtggaca t                                              21

<210> SEQ ID NO 49
<211> LENGTH: 21
<212> TYPE: DNA
<213> ORGANISM: Artificial Sequence
<220> FEATURE:
<223> OTHER INFORMATION: Targeting Sequence

<400> SEQUENCE: 49
aatgacgagg gcctggagtg t                                              21

<210> SEQ ID NO 50
<211> LENGTH: 21
<212> TYPE: DNA
<213> ORGANISM: Artificial Sequence
<220> FEATURE:
<223> OTHER INFORMATION: Targeting Sequence

<400> SEQUENCE: 50
aacatcacca tgcagattat g                                              21

<210> SEQ ID NO 51
<211> LENGTH: 21
<212> TYPE: DNA
<213> ORGANISM: Artificial Sequence
<220> FEATURE:
<223> OTHER INFORMATION: Targeting Sequence

<400> SEQUENCE: 51
aaacctcacc aaggccagca c                                              21

<210> SEQ ID NO 52
<211> LENGTH: 21
<212> TYPE: DNA
<213> ORGANISM: Artificial Sequence
<220> FEATURE:
<223> OTHER INFORMATION: Targeting Sequence

<400> SEQUENCE: 52
aaggccagca cataggagag a                                              21

<210> SEQ ID NO 53
<211> LENGTH: 21
<212> TYPE: DNA
<213> ORGANISM: Artificial Sequence
<220> FEATURE:
<223> OTHER INFORMATION: Targeting Sequence

<400> SEQUENCE: 53
aacaaatgtg aatgcagacc a                                              21

<210> SEQ ID NO 54
<211> LENGTH: 21
<212> TYPE: DNA
<213> ORGANISM: Artificial Sequence
<220> FEATURE:
<223> OTHER INFORMATION: Targeting Sequence

<400> SEQUENCE: 54
aaatgtgaat gcagaccaaa g                                              21

<210> SEQ ID NO 55
```

```
<211> LENGTH: 21
<212> TYPE: DNA
<213> ORGANISM: Artificial Sequence
<220> FEATURE:
<223> OTHER INFORMATION: Targeting Sequence

<400> SEQUENCE: 55
aatgcagacc aaagaaagat a                                              21

<210> SEQ ID NO 56
<211> LENGTH: 21
<212> TYPE: DNA
<213> ORGANISM: Artificial Sequence
<220> FEATURE:
<223> OTHER INFORMATION: Targeting Sequence

<400> SEQUENCE: 56
aaagaaagat agagcaagac a                                              21

<210> SEQ ID NO 57
<211> LENGTH: 21
<212> TYPE: DNA
<213> ORGANISM: Artificial Sequence
<220> FEATURE:
<223> OTHER INFORMATION: Targeting Sequence

<400> SEQUENCE: 57
aagaaagata gagcaagaca a                                              21

<210> SEQ ID NO 58
<211> LENGTH: 23
<212> TYPE: DNA
<213> ORGANISM: Artificial Sequence
<220> FEATURE:
<223> OTHER INFORMATION: Targeting Sequence

<400> SEQUENCE: 58
aagatagagc aagacaagaa aat                                            23

<210> SEQ ID NO 59
<211> LENGTH: 23
<212> TYPE: DNA
<213> ORGANISM: Artificial Sequence
<220> FEATURE:
<223> OTHER INFORMATION: Targeting Sequence

<400> SEQUENCE: 59
aagacaagaa aatccctgtg ggc                                            23

<210> SEQ ID NO 60
<211> LENGTH: 23
<212> TYPE: DNA
<213> ORGANISM: Artificial Sequence
<220> FEATURE:
<223> OTHER INFORMATION: Targeting Sequence

<400> SEQUENCE: 60 aagaaatcc ctgtgggcct tgc                                             23

<210> SEQ ID NO 61
<211> LENGTH: 23
<212> TYPE: DNA
<213> ORGANISM: Artificial Sequence
<220> FEATURE:
<223> OTHER INFORMATION: Targeting Sequence

<400> SEQUENCE: 61
```

-continued

```
aatccctgtg ggccttgctc aga                                              23

<210> SEQ ID NO 62
<211> LENGTH: 23
<212> TYPE: DNA
<213> ORGANISM: Artificial Sequence
<220> FEATURE:
<223> OTHER INFORMATION: Targeting Sequence

<400> SEQUENCE: 62
aagcatttgt ttgtacaaga tcc                                              23

<210> SEQ ID NO 63
<211> LENGTH: 23
<212> TYPE: DNA
<213> ORGANISM: Artificial Sequence
<220> FEATURE:
<223> OTHER INFORMATION: Targeting Sequence

<400> SEQUENCE: 63
aagatccgca gacgtgtaaa tgt                                              23

<210> SEQ ID NO 64
<211> LENGTH: 23
<212> TYPE: DNA
<213> ORGANISM: Artificial Sequence
<220> FEATURE:
<223> OTHER INFORMATION: Targeting Sequence

<400> SEQUENCE: 64
aaatgttcct gcaaaaacac aga                                              23

<210> SEQ ID NO 65
<211> LENGTH: 23
<212> TYPE: DNA
<213> ORGANISM: Artificial Sequence
<220> FEATURE:
<223> OTHER INFORMATION: Targeting Sequence

<400> SEQUENCE: 65
aatgttcctg caaaaacaca gac                                              23

<210> SEQ ID NO 66
<211> LENGTH: 23
<212> TYPE: DNA
<213> ORGANISM: Artificial Sequence
<220> FEATURE:
<223> OTHER INFORMATION: Targeting Sequence

<400> SEQUENCE: 66
aaaaacacag actcgcgttg caa                                              23

<210> SEQ ID NO 67
<211> LENGTH: 23
<212> TYPE: DNA
<213> ORGANISM: Artificial Sequence
<220> FEATURE:
<223> OTHER INFORMATION: Targeting Sequence

<400> SEQUENCE: 67
aaaacacaga ctcgcgttgc aag                                              23

<210> SEQ ID NO 68
<211> LENGTH: 23
<212> TYPE: DNA
```

```
<213> ORGANISM: Artificial Sequence
<220> FEATURE:
<223> OTHER INFORMATION: Targeting Sequence

<400> SEQUENCE: 68
aaacacagac tcgcgttgca agg                                             23

<210> SEQ ID NO 69
<211> LENGTH: 23
<212> TYPE: DNA
<213> ORGANISM: Artificial Sequence
<220> FEATURE:
<223> OTHER INFORMATION: Targeting Sequence

<400> SEQUENCE: 69
aacacagact cgcgttgcaa ggc                                             23

<210> SEQ ID NO 70
<211> LENGTH: 23
<212> TYPE: DNA
<213> ORGANISM: Artificial Sequence
<220> FEATURE:
<223> OTHER INFORMATION: Targeting Sequence

<400> SEQUENCE: 70
aaggcgaggc agcttgagtt aaa                                             23

<210> SEQ ID NO 71
<211> LENGTH: 23
<212> TYPE: DNA
<213> ORGANISM: Artificial Sequence
<220> FEATURE:
<223> OTHER INFORMATION: Targeting Sequence

<400> SEQUENCE: 71
aaacgaacgt acttgcagat gtg                                             23

<210> SEQ ID NO 72
<211> LENGTH: 23
<212> TYPE: DNA
<213> ORGANISM: Artificial Sequence
<220> FEATURE:
<223> OTHER INFORMATION: Targeting Sequence

<400> SEQUENCE: 72
aacgaacgta cttgcagatg tga                                             23

<210> SEQ ID NO 73
<211> LENGTH: 23
<212> TYPE: DNA
<213> ORGANISM: Artificial Sequence
<220> FEATURE:
<223> OTHER INFORMATION: Targeting Sequence

<400> SEQUENCE: 73
aagtggtccc aggctgcacc cat                                             23

<210> SEQ ID NO 74
<211> LENGTH: 23
<212> TYPE: DNA
<213> ORGANISM: Artificial Sequence
<220> FEATURE:
<223> OTHER INFORMATION: Targeting Sequence

<400> SEQUENCE: 74
aaggaggagg gcagaatcat cac                                             23
```

```
<210> SEQ ID NO 75
<211> LENGTH: 23
<212> TYPE: DNA
<213> ORGANISM: Artificial Sequence
<220> FEATURE:
<223> OTHER INFORMATION: Targeting Sequence

<400> SEQUENCE: 75
aagtggtgaa gttcatggat gtc                                               23

<210> SEQ ID NO 76
<211> LENGTH: 23
<212> TYPE: DNA
<213> ORGANISM: Artificial Sequence
<220> FEATURE:
<223> OTHER INFORMATION: Targeting Sequence

<400> SEQUENCE: 76
aaaatccctg tgggccttgc tca                                               23

<210> SEQ ID NO 77
<211> LENGTH: 21
<212> TYPE: DNA
<213> ORGANISM: Artificial Sequence
<220> FEATURE:
<223> OTHER INFORMATION: Sense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 77
accucaccaa ggccagcact t                                                 21

<210> SEQ ID NO 78
<211> LENGTH: 21
<212> TYPE: DNA
<213> ORGANISM: Artificial Sequence
<220> FEATURE:
<223> OTHER INFORMATION: Antisense strand
<220> FEATURE:
<221> NAME/KEY: misc_RNA
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 78
gugcuggccu uggugaggut t                                                 21

<210> SEQ ID NO 79
<211> LENGTH: 18
<212> TYPE: DNA
<213> ORGANISM: Artificial Sequence
<220> FEATURE:
<223> OTHER INFORMATION: Targeting sequence

<400> SEQUENCE: 79
ggctacgtcc agcgcacc                                                     18

<210> SEQ ID NO 80
```

```
<211> LENGTH: 21
<212> TYPE: DNA
<213> ORGANISM: Artificial Sequence
<220> FEATURE:
<223> OTHER INFORMATION: Targeting sequence

<400> SEQUENCE: 80
aaaccucacc aaagccagca c                                              21
```